United States Patent [19]

Romeo

[11] Patent Number: 5,684,144
[45] Date of Patent: Nov. 4, 1997

[54] ESCHERICHIA COLI CSRA GENE, PROTEIN ENCODED THEREBY, AND METHODS OF USE THEREOF

[75] Inventor: Tony Romeo, Arlington, Tex.

[73] Assignee: University of North Texas, Fort Worth, Tex.

[21] Appl. No.: 194,211

[22] Filed: Feb. 7, 1994

Related U.S. Application Data

[63] Continuation-in-part of Ser. No. 98,734, Jul. 28, 1993, abandoned.
[51] Int. Cl.$^6$ ............................ C12N 15/31; C12N 15/11
[52] U.S. Cl. .................. 536/23.7; 536/23.1; 435/172.3; 435/849; 435/69.2; 435/320.1; 435/252.3; 435/252.33; 935/9; 935/10; 935/11
[58] Field of Search .............................. 536/23.1, 23.7; 435/172.3, 849, 69.2, 320.1, 252.3, 252.33; 935/9, 11, 10

[56] References Cited

U.S. PATENT DOCUMENTS

| | | | |
|---|---|---|---|
| 3,817,837 | 6/1974 | Rubenstein et al. | 161/113 |
| 3,850,752 | 11/1974 | Schuurs et al. | 435/7.93 |
| 3,939,350 | 2/1976 | Kronick et al. | 250/365 |
| 3,996,345 | 12/1976 | Ullman et al. | 436/537 |
| 4,275,149 | 6/1981 | Litman et al. | 435/7.91 |
| 4,277,437 | 7/1981 | Maggio | 422/61 |
| 4,366,241 | 12/1982 | Tom et al. | 435/7.91 |
| 4,816,567 | 3/1989 | Cabilly et al. | 530/387.3 |
| 5,143,846 | 9/1992 | Huala et al. | 435/252.33 |

OTHER PUBLICATIONS

T. Romeo et al. "Molecular Characterization of the Pleiotropic..." Absts 93rd Am. Soc. Microbiol. Mt. p. 220 Abst. H–169 (May 1993).

Sabnis et al., "Pleiotropic regulation of central carbohydrate metabolism in Escherichia coli via the gene csrA" *J. Biol. Chem.* (1995) 270:29096–29104.

Yang et al., "Coordinate genetic regulation of glycogen catabolism and biosynthesis in *Escherichia coli* via the CsrA gene product" *J. Bacteriol.* (1996) 178:1012–1017.

Kolter, "Life and death in stationary phase" *ASM News* (1992) 58:75–79.

Matin, "The molecular basis of carbon–starvation–induced general resistance in *Escherichia coli*" *Mol. Microbiol.* (1991)5:3–10.

Matin et al., "Genetic basis of starvation survival in non-differentiating bacteria" *Ann. Rev. Microbiol.* (1989) 43:293–316.

Siegele et al., "Life after log" *J. Bacteriol.* (1992) 174:345–348.

Bohannon et al., "Stationary–phase–inducible 'Gearbox' promoters: Differential effects of katF mutations and role of $\sigma^{70}$" *J. Bacteriol.* (1991) 173:4482–4492.

Lange et al., "Identification of a central regulator of stationary–phase gene expression in *Escherichia coil*" *Mol. Microbiol.* (1991)5:49–59.

Schellhorn et al., "Regulation of katF and katE in *Escherichia coli* K–12 by weak acids" *J. Bacteriol.* (1992) 174:4769–4776.

Romeo et al., "Genetic regulation of glycogen biosynthesis in *Escherichia coil:* In Vivo effects of the catabolite repression and stringent response systems in glg gene expression" *Curr. Microbiol.* (1990) 21:131–137.

Romeo et al., "Genetic regulation of glycogen biosynthesis in *Escherichia coli:* In vitro effects of cyclic AMP and guanosine 5'–diphosphate 3'–diphosphate and analysis of in vivo transcripts" *J. Bacteriol.* (1989) 171:2773–2782.

Romeo et al., "Analysis of the *Escherichia coli* glycogen gene cluster suggests that catabolic enzymes are encoded among the biosynthetic genes" *Gene* (1988) 70:363–376.

(List continued on next page.)

*Primary Examiner*—Rebecca E. Prouty
*Attorney, Agent, or Firm*—Morrison & Foerster

[57] ABSTRACT

The invention includes a gene encoding csrA, the protein encoded thereby and methods of use thereof.

3 Claims, 22 Drawing Sheets

OTHER PUBLICATIONS

Yu et al., "α-glucan phosphorylase from *Escherichia coli*" *J. Biol. Chem.* (1988) 263:13706–13711.

Baecker et al., "Biosynthesis of bacterial glycogen" *J. Biol. Chem.* (1986) 261:8738–8743.

Preiss et al., "Physiology, biochemistry and genetics of bacterial glycogen synthesis" *Adv. Microbial Physiol.* (1989) 30:183–233.

Bridger et al., "relA gene control of bacterial glycogen synthesis" *Can. J. Biochem.* (1978) 56:403–406.

Dietzler et al., "Contribution of cyclic adenosine 3':5'-monophosphate to the regulation of bacterial glycogen synthesis in vivo" *J. Biol. Chem.* (1979) 254:8308–8317.

Dietzler et al., "Regulation of ADP-glucose synthetase, the rate–limiting enzyme of bacterial glycogen synthesis, by the pleiotropic nucleotides ppGpp and pppGpp" *Biochem. Biophys. Res. Comm.* (1977) 77:1459–1467.

Leckie et al., "Regulation of bacterial glycogen synthesis" *J. Biol. Chem.* (1983) 258:3813–3824.

Leckie et al., "Independence of cyclic AMP and relA gene stimulation of glycogen synthesis in intact *Escherichia coli* cells" *J. Bacteriol.* (1985) 161:133–140.

Taguchi et al., "Augmentation of glycogen synthesis under stringent control in *Escherichia coil*" *J. Biochem.* (1980) 88:379–387.

Costerton et al., "Bacterial biofilms in nature and disease" *Ann. Rev. Microbiol.* (1987) 41:435–464.

Marshall, "Biofilms: An overview of bacterial adhesion, activity, and control at surfaces" *ASM News* (1992)58:202–207.

Godowski et al., "Signal transduction and transcriptional regulation by glucocorticoid receptor–LexA fusion proteins" *Science* (1988) 241:812–816.

Kanehisa, "Use of statistical criteria for screening potential homologies in nucleic acid sequences" *Nucl. Acids Res.* (1984) 12:203–213.

Beaucage et al., "Deoxynucleoside phosphoramidites–a new class of key intermediates for deoxypolynucleotide synthesis" *Tetra. Lett.* (1981) 22:1859–1862.

Matteucci et al., "Synthesis of deoxyoligonucleotides on a polymer support" *J. Am. Chem. Soc.* (1981) 103:3185–3191.

Metzger et al., "The human oestrogen receptor functions in yeast" *Nature* (1988) 334:31–36.

European Patent Application No. 0073657 (Mar. 9, 1983).

Fiers et al., "Complete nucleotide sequence of SV40 DNA" *Nature* (1978) 273:113–120.

Huse et al., "Generation of a large combinatorial library of the immunoglobulin repertoire in phage lambda" *Science* (1989) 246:1275–1281.

Singer et al., "A collection of strains containing genetically linked alternating antibiotic resistance elements for genetic mapping of *Escherichia coli*" *Microbiol. Rev.* (1989) 53:1–24.

Wu, "A model for three–point analysis of random general transduction" *Genetics* (1966) 54:405–410.

Feinberg et al., "A technique for radiolabeling DNA restriction endonuclease fragments to high specific activity" *Anal. Biochem.* (1983) 132:6–13.

Kohara et al., "The physical map of the whole *E. coli* chromosome: Application of a new strategy for rapid analysis and sorting of a large genomic library" *Cell* (1987) 50:495–508.

Wanner et al., "Physiological regulation of a decontrolled lac operon" *J. Bacteriol.* (1977) 130:212–222.

Way et al., "New Tn10 derivatives for transposon mutagenesis and for construction of lacZ operon fusions by transposition" *Gene* (1984) 32:369–379.

Haziza et al., "Nucleotide sequence of the asd gene of *Escherichia coli*: Absence of a typical attenuation signal" *EMBO J.* (1982)1:379–384.

Gyllensten, "Direct sequencing of in vitro amplified DNA" *PCR Technology: Principles and Applications for DNA Amplification* Erlich, H.A., ed., (1989), M Stockton Press, New York, pp. 45–60.

Henikoff, "Unidirectional digestion with exonuclease III creates targeted breakpoints for DNA sequencing" *Gene* (1984) 28:351–359.

Sanger et al., "DNA sequencing with chain–terminating inhibitors" *Proc. Natl. Acad. Sci. USA* (1977) 74:5463–5467.

Marck, "'DNA strider': A 'C' program for the fast analysis of DNA and protein sequences on the Apple Mcintosh family of computers" *Nucl. Acids Res.* (1988) 16:1829–1836.

Kyte et al., "A simple method for displaying the hydropathic character of a protein" *J. Mol Biol.* (1982) 157:105–132.

Putney et al., "Primary structure of a large aminoacyl–tRNA synthetase" *Science* (1981) 213:1497–1501.

Shine et al., "The 3'–terminal sequence of *Escherichia coil* 16S ribosomal RNA: Complementarity to nonsense triplets and ribosome binding sites" *Proc. Natl. Acad. Sci. USA* (1974) 71:1342–1346.

Komine et al., "Genomic organization and physical mapping of the transfer RNA genes in *Escherichia coli* K12" *J. Mol. Biol.* (1990) 212:579–598.

Petersen et al., "Messenger RNA recognition in *Escherichia coli*: A possible second site of interaction with 16S ribosomal RNA" *EMBO J.* (1988) 7:3957–3962.

Chamberlain, "Fluorographic detection of radioactivity in polyacrylamide gels with the water–soluble fluor, sodium salicylate" *Anal. Biochem.* (1979) 98:132–135.

Hengge–Aronis et al., "Identification and molecular analysis of glgS, a novel growth–phase–regulated and rpoS–dependent gene involved in glycogen synthesis in *Escherichia coli*" *Mol. Microbiol.* (1992) 6:1877–1886.

Esnouf et al., "Triosephosphate isomerase from chicken and rabbit muscle" *Meth. Enzymol.* (1982) 89:579–583.

Pompliano et al., "Stabilization of a reaction intermediate as a catalytic device: Definition of the functional role of the flexible loop in triosephosphate isomerase" *Biochem.* (1990) 29:3186–3194.

Pradel et al., "Utilization of exogenous glucose–1–phosphate as a source of carbon or phosphate by *Escherichia coli* K12: Respective roles of acid glucose–1–phosphatase, hexose–phosphate permease, phosphoglucomutase and alkaline phosphatase" *Res. Microbiol.* (1991) 142:37–45.

Adhya et al., "Phosphoglucomutase mutants of *Escherichia coli* K–12" *J. Bacteriol.* (1971) 108:621–626.

Fraenkel et al., "Fructose–1, 6–diphosphatase and acid hexose phosphatase of *Escherichia coil*" *J. Bacteriol.* (1965) 90:837–842.

Fraenkel et al., "Glucose and gluconate metabolism in an *Escherichia coli* mutant lacking phosphoglucose isomerase" *J. Bacteriol.* (1967) 93:1571–1578.

Romeo et al., "Genetic and physical mapping of the regulatory gene csrA on the *Escherichia coli* K–12 chromosome" *J. Bacteriol.* (1993) 175:5740–5741.

Romeo et al., "Identification and molecular characterization of csrA, a pleiotropic gene from *Escherichia coli* that affects glycogen, biosynthesis, gluconeogenesis, cell size, and surface properties" *J. Bacteriol.* (1993)175:4744–4755.

Romeo et al., "A simple method for cloning genes involved in glucan biosynthesis: Isolation of structural and regulatory genes for glycogen synthesis in *Escherichia coli*" *Gene* (1991)108:23–29.

```
        870     (alaS)
AGTGTGAAAGGGCTGGGTCAGCGCGAAATTGCAATAATATAAGGCGTCAGGCAATGCCGTGG    60
 S   V   K   G   W   V   S   A   K   L   Q  OCH
                                    DdeI
ACTCGCTTCACGGCATTCGCATTAACGCTATCGACAACGATAAAGTCAGGTTGAAGTTGT    120

GTATATCGGCTAAACTTAGGTTTAACAGAATGTAATGCCATGACTGCTTAGATGTAATGT    180

GTTTGTCATTGCTTACTTTTTGGCGTTATATGGATAATGCCGGGATACAGAGAGACC       240
                      S.D.      1 (csrA)
CGACTCTTTTAATCTTTCAAGGAGCAAAGAATGCTGATTCTGACTCGTCGAGTTGGGTGAG   300
                                M   L   I   L   T   R   R   V   G   E
                                                                10
ACCCTCATGATTGGGGATGAGGTCACCGTGACAGTTTTAGGGGTAAAGGGCAACCAGGTA    360
 T   L   M   I   G   D   E   V   T   V   T   V   L   G   V   K   G   N   Q   V
        20                                              30
CGTATTGGGCGTAAATGCCCCGAAGGAAGTTTCTGTTCACCGTGAAGAGATCTACCAGCGT    420
 R   I   G   V   N   A   P   K   E   V   S   V   H   R   E   E   I   Y   Q   R
 →                                                  50
        40
ATCCAGGCTGAAAAATCCCAGTCCCAGTCAGTTACTAATCTTTCCGGCTCTCATCTTTATCG   480
 I   Q   A   E   K   S   Q   S   Q   S   S   Y  OCH
                                            60

GTGAGACGCCACCCTCAAAATTTCTCACTCTTTTTGCTTTACTCCCGTTC              540

ATTCAACTTAAGTCTCCATTTTTTGCATTACTACTATCTGTCAGACCTCCATTCTTCTG    600

TTGATAAAACACTCTTTTTGACGTTTTACAGACTAATTGAACGTGAAGTGTGCAAACGA    660
                                -10
TAAAAGTGTAGGAAAAATTGTTTGACTTATAAGTCTCAGAAAGTAATAT   709
    -35   (serv)    DdeI
```

FIG. 9

| PLASMID | DELETIONS [Δ] | CHANGE IN DNA (bp) | CHANGE IN ORF(aa) |
|---|---|---|---|
| pCSR 10 | | – | – |
| pCSR L1 | [Δ] | -57 | 0 |
| pCSR D1-L | [ Δ ] | -117 | -8, +24 |
| pCSR D3 | [ Δ ] | -159 | -21, +23 |
| pCSR D1-D | [ Δ ] | -277 | -16, +4 |

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 709 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..33

( i x ) FEATURE:
        ( A ) NAME/KEY: CDS
        ( B ) LOCATION: 271..453

( x i ) SEQUENCE DESCRIPTION: SEQ ID NO:1:

```
AGT GTG AAA GGC TGG GTC AGC GCG AAA TTG CAA  TAATATAAGC GTCAGGCAAT         53
Ser Val Lys Gly Trp Val Ser Ala Lys Leu Gln
 1               5                  10

GCCGTGGACT CGCTTCACGG CATTCGCATT AACGCTATCG ACAACGATAA AGTCAGGTTG          113
```

-continued

```
AAGTTGTGTA TATCGGCTAA ACTTAGGTTT AACAGAATGT AATGCCATGA CTGCTTAGAT      173

GTAATGTGTT TGTCATTGCT TACTTTTTGG CGTTATATGA TGGATAATGC CGGGATACAG      233

AGAGACCCGA CTCTTTTAAT CTTTCAAGGA GCAAAGA ATG CTG ATT CTG ACT CGT      288
                                         Met Leu Ile Leu Thr Arg
                                          1                   5

CGA GTT GGT GAG ACC CTC ATG ATT GGG GAT GAG GTC ACC GTG ACA GTT       336
Arg Val Gly Glu Thr Leu Met Ile Gly Asp Glu Val Thr Val Thr Val
            10                  15                  20

TTA GGG GTA AAG GGC AAC CAG GTA CGT ATT GGC GTA AAT GCC CCG AAG       384
Leu Gly Val Lys Gly Asn Gln Val Arg Ile Gly Val Asn Ala Pro Lys
        25                  30                  35

GAA GTT TCT GTT CAC CGT GAA GAG ATC TAC CAG CGT ATC CAG GCT GAA       432
Glu Val Ser Val His Arg Glu Glu Ile Tyr Gln Arg Ile Gln Ala Glu
        40                  45                  50

AAA TCC CAG CAG TCC AGT TAC TAATCTTTCC GCGTCTCATC TTTATCGGTG          483
Lys Ser Gln Gln Ser Ser Tyr
 55                  60

AGACGCACCC TCAAAATTTC TCCTTCACTC TATAGTCTTT TCGCTTTACT CCCGTTCATT      543

CAACTTAAGT CTCCATTTTT TTGCATTACT ACTATCTGTC AGACCTCCAT TCTTCTGTTG      603

ATAAAACACT CTTTTTGACG TTTTTACAGA CTAATTGAAC GTGAAGTGTG CAAACGATAA      663

AAGTGTAGGA AAAATTGTTT GACTTATAAG TCTCAGAAAG TAATAT                    709
```

(2) INFORMATION FOR SEQ ID NO:2:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:2:

```
Ser Val Lys Gly Trp Val Ser Ala Lys Leu Gln
 1               5                   10
```

(2) INFORMATION FOR SEQ ID NO:3:

(i) SEQUENCE CHARACTERISTICS:
        (A) LENGTH: 61 amino acids
        (B) TYPE: amino acid
        (D) TOPOLOGY: linear (ii) MOLECULE TYPE: protein (xi) SEQUENCE DESCRIPTION: SEQ ID NO:3:

```
Met Leu Ile Leu Thr Arg Arg Val Gly Glu Thr Leu Met Ile Gly Asp
 1               5                   10                  15

Glu Val Thr Val Thr Val Leu Gly Val Lys Gly Asn Gln Val Arg Ile
                20                  25                  30

Gly Val Asn Ala Pro Lys Glu Val Ser Val His Arg Glu Glu Ile Tyr
            35                  40                  45

Gln Arg Ile Gln Ala Glu Lys Ser Gln Gln Ser Ser Tyr
         50                  55                  60
```

ESCHERICHIA COLI CSRA GENE, PROTEIN ENCODED THEREBY, AND METHODS OF USE THEREOF

CROSS-REFERENCE TO RELATED APPLICATIONS

This application is a continuation-in-part of U.S. patent application Ser. No. 08/098,734 now abandoned which was filed on Jul. 28, 1993, which application is included herein by reference.

ACKNOWLEDGEMENT OF GOVERNMENT SUPPORT

This invention was made with government support under grant number MCB-9218796, awarded by the National Science Foundation. The government has certain rights in the invention.

TECHNICAL FIELD

This invention is related to the field of microbiology. Specifically, the invention relates to alteration of metabolic pathways in *Escherichia coli* and other bacteria.

BACKGROUND ART

Bacteria grown in the laboratory have three stages of growth, the lag phase in which little growth occurs, the log phase in which exponential growth occurs and the stationary phase in which growth ceases. During the transition into stationary phase, bacteria acquire numerous new physiological properties which enhance their ability to compete and survive under suboptimal conditions. For reviews, see Kolter (1992) ASM News 58:75–79; Matin (1991) *Mol. Microbiol.* 5:3–10; Matin et al. (1989) *Ann. Rev. Microbiol.* 43:293–316; and Siegele and Kolter (1992) *J. Bacteriol.* 174:345–348. In *Escherichia coli* the induction of several genes and operons in the stationary phase requires a putative sigma factor, katF or rpoS. Bohannon et al. (1991) *J. Bacteriol.* 173:4482–4492; Lange and Hengge-Aronis (1991) *Mol. Microbiol.* 5:49–59; Matin (1991); and Schellhorn and Stones (1992) *J. Bacteriol.* 174:4769–4776. The expression of stationary-phase genes such as mcbA for microcin production and glgCA for glycogen synthesis do not require katF. Bohannon et al. (1991).

Previous studies of factors that control the glycogen biosynthesis genes in *E. coli* showed that cyclic AMP (cAMP), cAMP receptor protein, and guanosine 3'-bisphosphate 5'-bisphosphate (ppGpp) stimulate the expression of the genes for the essential enzymes of the glycogen pathway, glgC (encoding ADPglucose pyrophosphorylase [EC 2.7.7.27]) and glgA (encoding glycogen synthase [EC 2.4.1.21]) which are apparently cotranscribed in an operon, glgCAY. Romeo et al. (1990) *Curr. Microbiol.* 21:131–137; and Romeo and Priess (1989) *J. Bacteriol.* 171:2773–2782. This operon also includes the gene encoding the catabolic enzyme glycogen phosphorylase [E.C 2.4.1.1], glgY or glgP. Romeo et al. (1988) *Gene* 70:363–376; and Yu et al. (1988) *J. Biol. Chem.* 263:13706–13711.

The gene glgB (encoding glycogen branching enzyme [EC 2.4.1.18]) is located upstream from glgCAY, apparently in an operon, glgBX, that includes a gene encoding a second catabolic enzyme. Baecker et al. (1986) *J. Biol. Chem.* 261:8738–8743; and Romeo et al. (1988). Although the expression of the three biosynthetic genes is induced in stationary phase, glgB is transcribed independently of glgCA and is not regulated by cAMP-cAMP receptor protein or ppGpp. Preiss and Romeo (1989)*Adv. Microb. Physiol.* 30:183–233; and Romeo and Preiss (1989). Four stationary-phase-induced transcripts have been mapped within the 0.5 kb upstream noncoding region of the glgC gene from *E. coli*, implying complex transcriptional regulation of glgCA. Romeo and Preiss (1989).

It would be highly advantageous to inhibit the metabolic pathway for glycogen biosynthesis and later reactions of gluconeogenesis in bacterial host cells, while stimulating anaplerotic reactions such as phosphoenolpyruvate carboxykinase in order to channel more carbon atoms into desired products such as aromatic amino acids.

DISCLOSURE OF THE INVENTION

The invention is directed to the csrA gene, the protein encoded thereby and methods of use thereof. Modulation of csrA gene expression is useful in regulating expression of downstream metabolic products and alone, or in conjunction with other mutations, is suitable for use in production of bacterial products.

BRIEF DESCRIPTION OF THE DRAWINGS

FIG. 9(SEQ ID NO:1, SEQ ID NO:2 and SEQ ID NO:3). depicts the nucleotide sequence of the csrA gene and the deduced amino acid sequence of the open reading frame (ORF) encoded therein. An arrow marks the site of the TR1-5 insertion mutation, which is between 421 and 422 bp. The DdeI sites used in subcloning csrA into pUC19 to generate pCSR10 are located at 168 and 698 bp.

FIGS. 11A, 11B and 11C depict in vitro expression and complementation analysis of csrA: evidence that csrA encodes a 61 amino acid polypeptide that inhibits glycogen biosynthesis. A series of deletions from the plasmid pCSR10 was constructed and characterized by nucleotide sequencing. The extent of each of the deletions with respect to the nucleotide sequence shown in FIG. 10 is as follows: pCSR-L1, 549 to 604; pCSR-D1-L, 431 to 547, pCSR-D3, 389 to 547; and pCSR-D1-D, from 405 through the KpnI site of the pUC19 vector. (A) The extent of each deletion, relative to the proposed ORF for csrA (indicated by an arrow), is shown schematically. The effect of each deletion on the size of the ORF is also shown. (B) pCSR10, pUC19, and the deletion derivatives were transformed into TR1-5BW3414 (csrA::kan) and were tested for endogenous glycogen by iodine staining. (C) Analysis of proteins synthesized in S-30-coupled transcription translation reactions with pUC19, pCSR10, pCSR-D1-L, and pCSR-D1-D as genetic templates. Protein standards utilized as molecular mass markers were ovalbumin (43 kDa), α-chymotrypsinogen (25.7 kDa), β-lactoglobulin (18.4 kDa), cytochrome c (12.3 kDa), bovine trypsin inhibitor (6.2 kDa), and insulin (A and B chains [3 kDa]). aa stands for amino acids.

MODES FOR CARRYING OUT THE INVENTION

Figure 1:
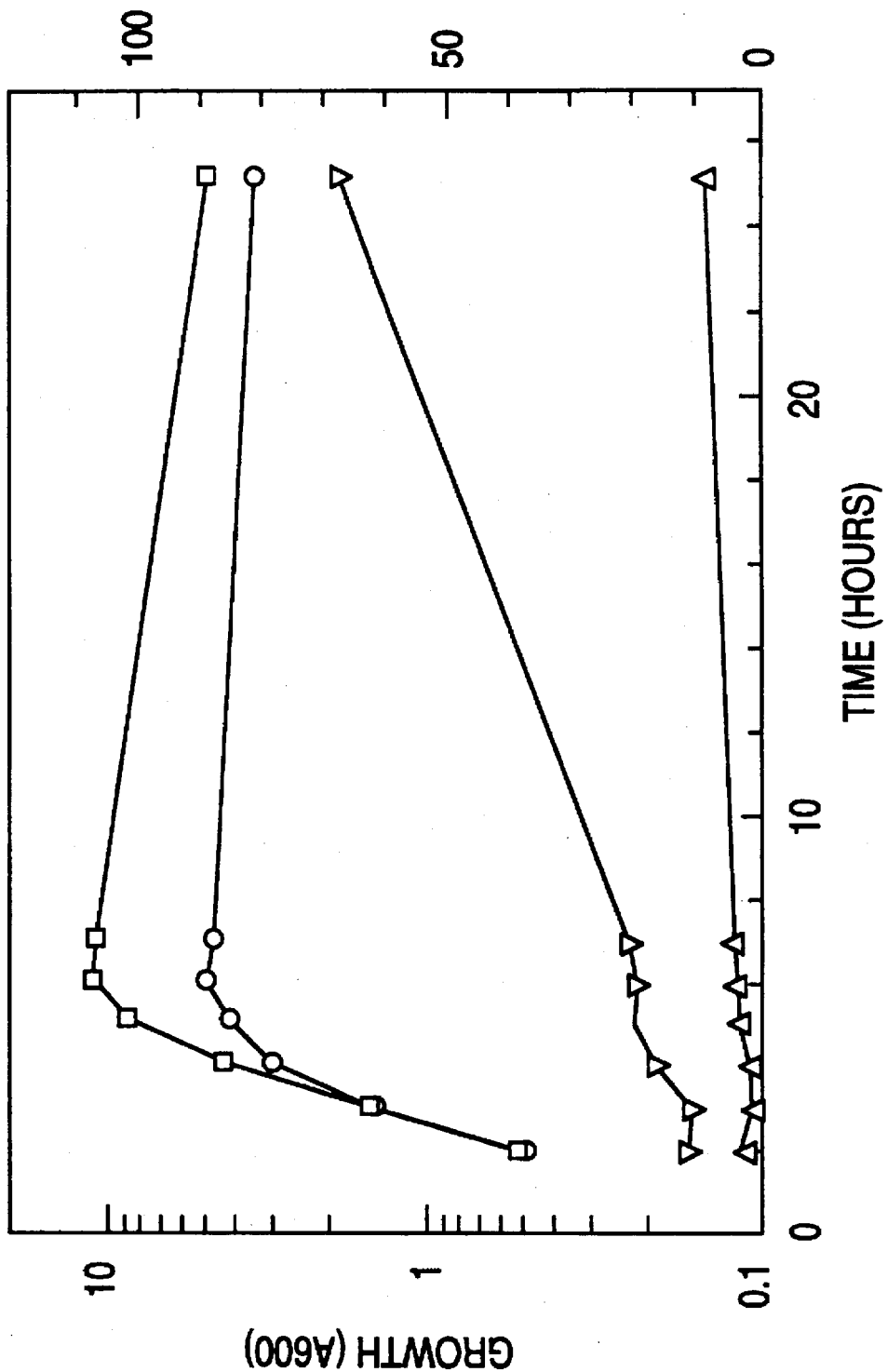
FIG. 1 is a graph depicting levels of expression of a glgC'-'lacZ translational fusion in BW3414 and TR1-5BW3414. Sample identities are as follows: circles, and squares, respectively, growth ($A_{600}$) of cultures for BW3414 and TR1-5BW3414; triangles, β-galactosidase activity, with apices facing up or down for BW3414 or TR1-5BW3414, respectively.

A few global regulatory factors mediate many of the extensive changes in gene expression that occur as E. coli enters the stationary phase. One of the metabolic pathways that is transcriptionally activated in the stationary phase is the pathway for glycogen biosynthesis. Described herein is the identification, cloning, and molecular characterization of a gene csrA, which exerts pleiotropic effects by not only controlling glycogen biosynthesis but also controlling gluconeogenesis and exhibiting effects on cell size and surface (adherence) properties. E. coli csrA thus encodes a global regulatory factor.

The nucleotide sequence of E. coli csrA is presented in FIG. 9(SEQ ID NO:1). A plasmid clone of the native csrA gene capable of expressing the 61 amino acid csrA gene product strongly inhibits glycogen accumulation and affects the ability of cells to utilize certain carbon sources for growth. The regulated expression of the csrA gene and its gene product are useful for enhancing expression of products produced by alternative pathways. Such products include but are not limited to antibiotics, metabolites, organic acids, amino acids and a wide variety of industrially important compounds produced in bacterial fermentation systems.

E. coli csrA and its effects

Glycogen synthesis is one of a number of metabolic pathways that are induced in bacteria, for example, E. coli in the stationary phase. The accumulation of glycogen in the early stationary phase reflects at least two levels of regulation, allosteric regulation of the committed step of the biochemical pathway and enhanced expression of the structural genes for the pathway.

As shown in the Examples below, the csrA gene encodes a trans-acting negative regulator of the expression of both glgC and glgB, essential enzymes of the glycogen pathway. The csrA mutation is pleiotropic, indicating that csrA encodes a global regulatory factor.

Glycogen synthesis is negatively controlled via the effects of the gene product of csrA (CsrA) on the expression of the operons glgCAY(P) and glgBX. A csrA::kan[r] transposon insertion increased the expression of glgC and glgB; however, it did not temporally alter the induction or change the shape of the induction curves for these genes, indicating that csrA functions in addition to the factors that mediate the growth phase response.

The discovery of csrA has led to the identification of a third system for the regulation of glycogen biosynthesis via glgCA expression. This third system may be contrasted with the two other known systems, cAMP-cAMP receptor protein and ppGpp, which are positive regulators of glgCA and of glycogen synthesis. Romeo et al. (1990); Romeo and Preiss (1989); Bridger and Paranchych (1978) Can. J. Biochem. 56:403–406; Dietzler et al. (1979) J. Biol. Chem. 254:8308–8317; Dietzler et al. (1977) Biochem. Biophys. Res. Commun. 77:1459–1467; Leckie et al. (1983) J. Biol. Chem. 258:3813–3824; Leckie et al. (1985) J. Bacteriol. 161:133–140; and Taguchi et al. (1980) J. Biochem. 88:379–387.

The physiological role played by these systems may be to establish an intrinsic metabolic capacity for glycogen synthesis in response to nutritional status. The effects of other regulatory factors, such as the allosteric effectors fructose-1,6-bisphosphate and AMP, may be superimposed upon this intrinsic metabolic capacity. These regulatory systems have been shown not to be involved in glgCA expression; the nitrogen starvation system, mediated by NtrC and NtrA or $\sigma^{\mathcal{N}}$; heat shock, mediated by $\sigma^{32}$; and the katF-dependent system Preiss and Romeo (1989); Romeo and Preiss (1989); and Hengge-Aronis and Fischer (1992) *Mol. Microbiol.* 6:1877–1886. These results indicate that the effects of csrA are not indirectly mediated via these global systems.

As shown in more detail in the Examples presented below, csrA is involved in the regulation of gluconeogenesis. The TR1-5 mutation in csrA caused overexpression of the gene pckA, as evidenced by a twofold overexpression of a pckA-lacZ transcriptional fusion. The TR1-5 mutation, however, did not alter the shape of the pckA-lacZ induction curve, a response that was similar to that of the glg genes.

The plasmid pCSR10 overexpresses the csrA gene product, as indicated by in vitro expression studies and by the strong inhibitory effect of the csrA gene product on glycogen synthesis. Cells containing pCSR10 did not grow on gluconeogenic substrates in M9 minimal medium. Since pckA was overexpressed in the TR1-5 mutant, the overexpression of csrA in these cells may cause excessive repression of pckA (and possibly other genes involved in gluconeogenesis), resulting in the failure of these cells to grow with gluconeogenic substrates on M9 medium. Indeed, pSCR10-containing cells grew poorly on MOPS-supplemented supplemented medium with succinate as a major carbon source, indicating that csrA may affect succinate uptake.

The gene pckA encodes phosphoenolpyruvate (PEP) carboxykinase, which produces PEP, a precursor of aromatic amino acids (tyrosine, phenylalanine, and tryptophan) and other metabolic products. The TR1-5 mutation or any other mutations that inactivate or down-regulate csrA may be used to increase PEP levels, resulting in increased synthesis of these aromatic amino acids. Aromatic amino acids, which are commercially produced using *E. coli* cultures, have numerous commercial uses, including the production of aspartame (Nutrisweet™).

Figure 13A:
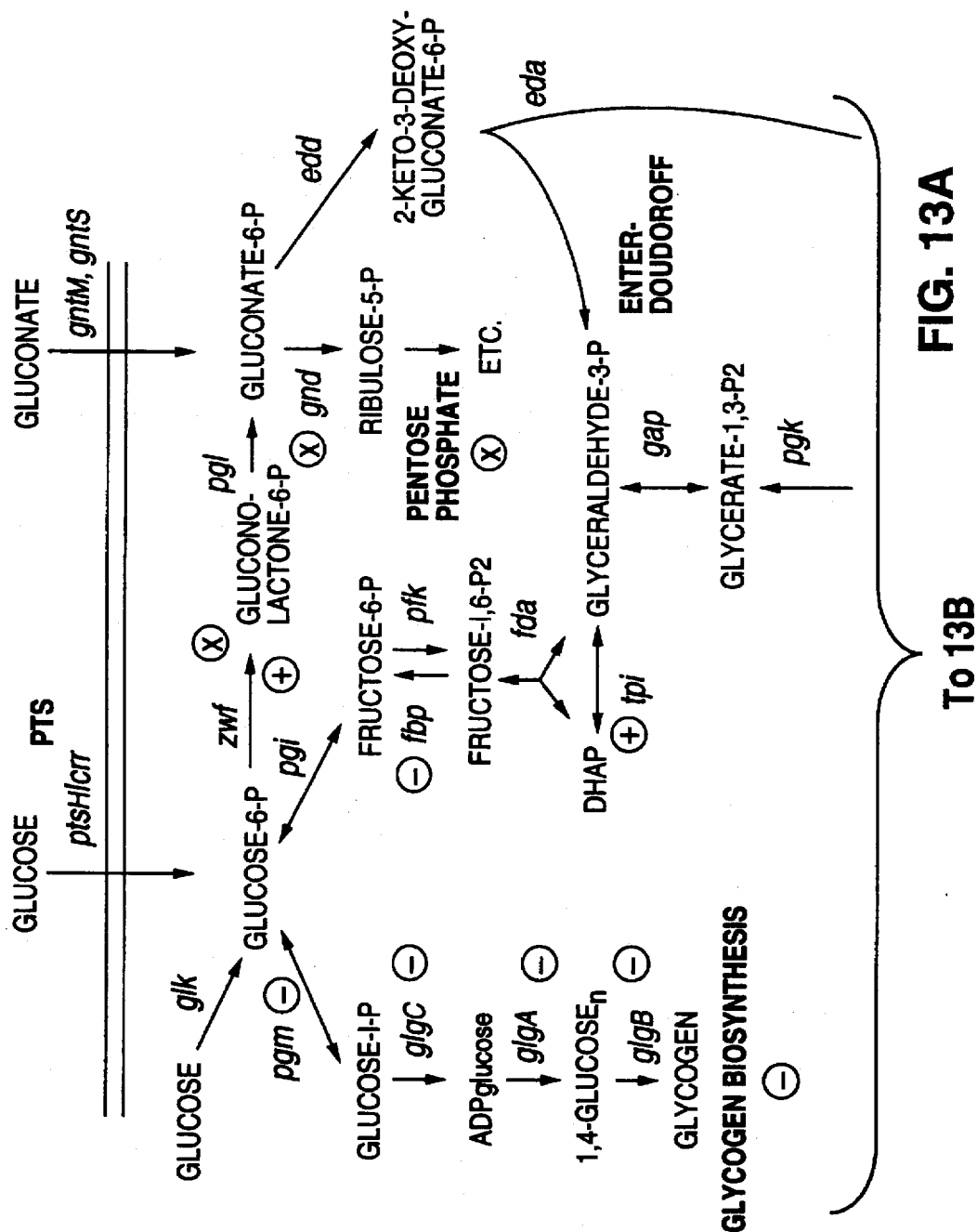
FIG. 13 is a metabolic chart depicting the regulatory effects of csrA on intermediary carbon metabolism.
Figure 13B:
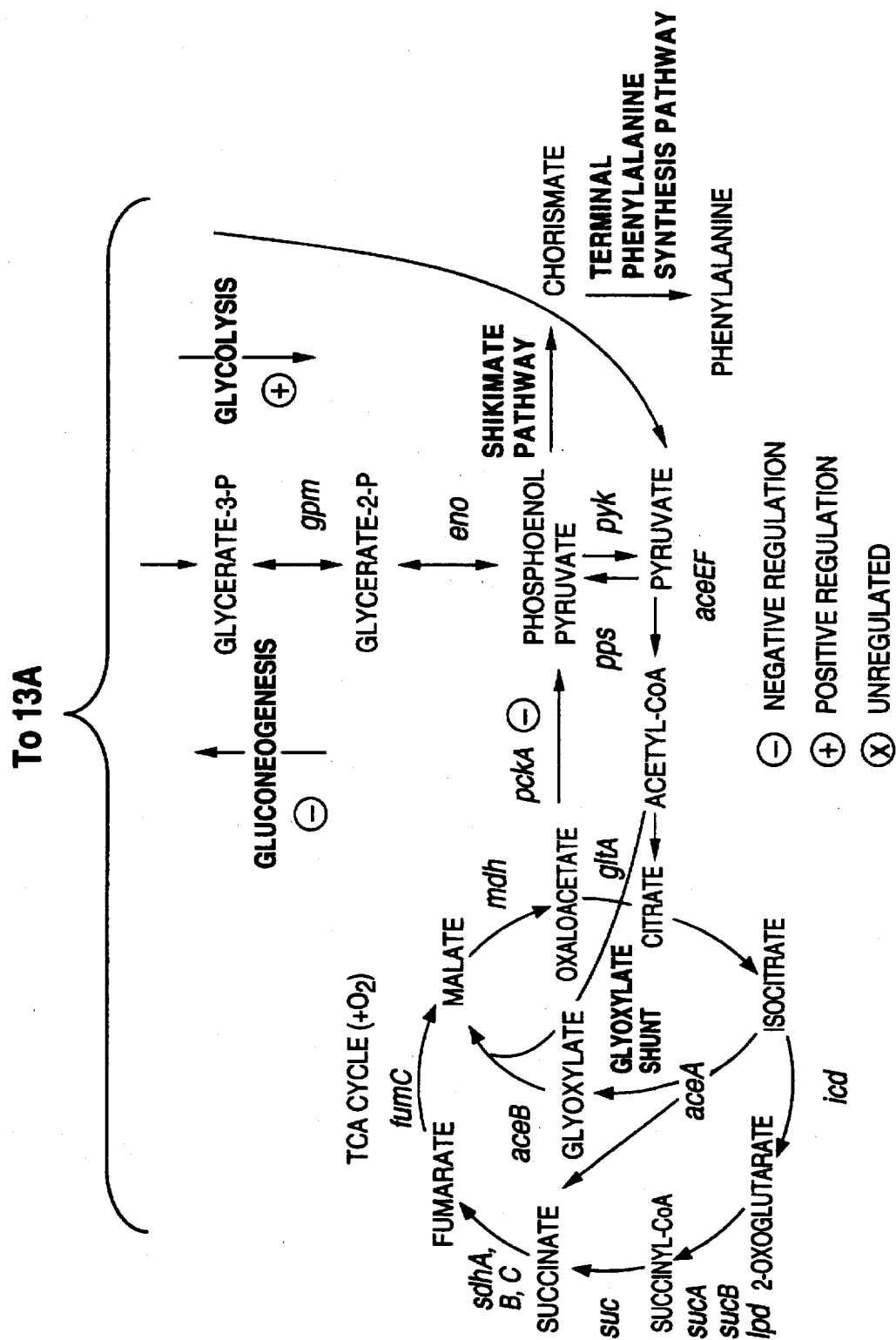

Further "metabolic engineering" should lead to even greater yields of any or all of these amino acids or other desired products. FIG. 13 depicts the regulatory effects of csrA on intermediary carbon metabolism. For example, PEP is a precursor of glucose via gluconeogenesis. Glucose is, in turn, a precursor of glycogen. Gluconeogenesis and glycogen synthesis are also elevated in the csrA mutant and would compete with the shikimate pathway, which is involved in the synthesis of aromatic amino acids. Therefore, in order to further optimize carbon flow into the desired products, engineering of gluconeogenesis, glycogen biosynthesis and possibly other pathways would be desirable. A mutation in fbp, which encodes fructose-1,6-bisphosphatase, would prevent gluconeogenesis from proceeding beyond the synthesis of fructose-1,6-bisphosphate. A mutation in glgC (ADP-glucose pyrophosphorylase) or glgA (glycogen synthase) would prevent residual glucose or glucose derivatives derived from the media or generated within the cell from being used for glycogen synthesis. Each of these mutations are already known and can be introduced into a cell either by P1 transduction from existing mutants or new mutations can be generated in appropriate commercial *E. coli* strains. The synthesis of a desired amino acid can be further enhanced by introducing mutations which block the synthesis of one or two of the three aromatic acids.

It has now been shown that csrA inhibits the expression of four genes involved in glycogen biosynthesis (glgB, C, A, S) pgm (phosphoglucomutase) and two genes in gluconeogenesis (pckA and fbp) and enhances the expression of the glycolytic genes tpi (trios-phosphate isomerase) and pgi (phosphoglucose isomerase). Since csrA is a global regulatory factor, it may affect the other genes of gluconeogenesis and genes in other pathways. By altering csrA expression and/or function, the levels of several enzymes can be simultaneously affected, more effectively channelling carbon flux into desired pathways than the more standard approach of placing an enzyme of a pathway under the control of a regulated promoter. It is likely that csrA regulates pps, which encodes PEP synthase. Therefore, TR1-5 or other mutations in csrA would increase carbon flux into PEP at a rate even greater than would be predicted on the basis of its effects on pckA alone.

It has now been shown that it is feasible to alter the levels of intermediate metabolic products by regulation of csrA expression. The production of the amino acid including, but not limited to, phenylalanine can be enhanced. In order to modulate downstream metabolic events, csrA is inactivated for instance by introduction of the csrA::kanR mutation, TR1-5. This enhances the expression of glycogen genes and genes for gluconeogenesis. The genes pckA (phosphoenolpyruvate carboxykinase) and perhaps pps (phosphoenolpyruvate synthase) will be expressed at higher levels, increasing the production of phosphoenolpyruvate, which is a direct precursor of phenylalanine. By introducing secondary mutations which inactivate one or more structural genes for glycogen synthesis (e.g. glgC or glgA) and disrupt fbp (fructose-1,6-bisphosphatase), which is needed for a later step of the gluconeogenesis pathway, the unwanted flow of carbon into glycogen that would be enhanced in the csrA mutant will be prevented.

The production of a desired product produced by a biosynthetic pathway not directly regulated by csrA can likewise be increased by blocking the carbon flux into a competing pathway which is controlled by csrA.

Surprisingly csrA affects cell surface properties. Glycogen is an endogenous polymer, and the effect of csrA on adherence is not due to its effect on glycogen synthesis, since transduction of the TR1-5 allele into the glycogen-deficient strain G6MD3 also caused this strain to become adherent. However, the surface molecule(s) that promotes adherence in the TR1-5 mutant remains undefined. The adherence to and colonization of surfaces by bacteria with the formation of a biofilm, as observed for TR1-5, is affected by nutrient availability and other environmental conditions and is an alternative strategy for cell survival. For reviews, see Costerton et al. (1987) *Annu. Rev. Microbiol.* 41:435–464; and Marshall (1992) *ASM News* 58:202–207.

CsrA Polypeptides

A "CsrA polypeptide" is a polypeptide encoded by the *E. coli* csrA gene or a polypeptide substantially homologous thereto and having CsrA activity.

Encompassed by the claimed CsrA polypeptides are variants of CsrA in which there have been trivial substitutions, deletions, insertions or other modifications of the native CsrA polypeptide which substantially retain CsrA characteristics, particularly silent or conservative substitutions. Silent nucleotide substitutions are changes of one or more nucleotides which do not change any amino acid of CsrA. Conservative substitutions include substitutions in the following groups: glycine, alanine; valine, isoleucine, leucine; aspartic acid, glutamic acid; asparagine, glutamine; serine, threonine; lysine, arginine; and phenylalanine, tyrosine. Such conservative substitutions are not expected to interfere with CsrA biochemical activity, particularly when they occur in structural regions (e.g., alpha helices or beta pleated sheets) of the polypeptide, which may be predicted by standard computer analysis of the amino acid sequence of E. coli CsrA.

The polypeptides of the present invention may be coupled to a solid phase support, e.g., nitrocellulose, nylon, column packing materials (e.g., Sepharose beads), magnetic beads, glass wool, cells, or other substrates.

The polypeptides of the present invention will typically be made by recombinant nucleic acid methods, as described below, but may be chemically synthesized. Techniques for chemical synthesis of polypeptides are described, for example, in Merrifield (1963) *J. Amer. Chem. Soc.* 85:2149–2156.

Substantial homology or identity.

The term "substantial homology" or "substantial identity", when referring to polypeptides, indicates that the polypeptide or protein in question exhibits at least about 30% identity with an entire naturally occurring protein or a portion thereof, usually at least about 70% identity, and preferably at least about 95% identity. Homologous CsrA proteins are also encompassed by the scope of the invention. Homologous proteins are generally encoded by homologous genes as described below, and retain significant amino acid residue identity to the CsrA protein. Such proteins may be expressed by other organisms such as bacteria, yeast and higher order organisms such as mammals. Various methods of determining amino acid residue identity are known in the art. Homologous polypeptides may be obtained by in vitro synthesis by expressing genes derived from other bacteria or by mutagenizing a gene encoding CsrA. Use of the terms CsrA or CsrA encompass homologous genes and proteins respectively.

Polypeptide homology is typically measured using sequence analysis software. See, e.g., Sequence Analysis Software Package of the Genetics Computer Group, University of Wisconsin Biotechnology Center, 1710 University Avenue, Madison, Wis. 53705. Protein analysis software matches similar sequences using measure of homology assigned to various substitutions, deletions, substitutions, and other modifications.

"Isolated"

The terms "isolated," "pure," "substantially pure," and "substantially homogeneous" are used interchangeably to describe a protein or polypeptide which has been separated from components which naturally accompany it. A monomeric protein is substantially pure when at least about 60 to 75% of a sample exhibits a single polypeptide sequence. A substantially pure protein typically comprises about 60 to 90% by weight of a protein sample, more usually about 95%, and preferably will be over about 99% pure.

Protein purity or homogeneity may be indicated by a number of means, such as polyacrylamide gel electrophoresis of a protein sample, followed by visualizing a single polypeptide band upon staining the gel. For certain purposes higher resolution may be provided by using high performance liquid chromatography (HPLC) or other means well known in the art for purification.

A CsrA protein is "isolated" when it is substantially separated from the contaminants which accompany it in its natural state. Thus, a polypeptide which is chemically synthesized or expressed as a recombinant protein, i.e., an expression product of an isolated and manipulated genetic sequence, is considered isolated. A recombinant polypeptide is considered "isolated" even if expressed in a homologous cell type.

Protein purification

A CsrA polypeptide may be purified from cells in which it is produced by any of the purification methods known in the art. For example, such polypeptides may be purified by immunoaffinity chromatography employing, e.g., the antibodies provided by the present invention. Various methods of protein purification include, but are not limited to, those described in *Guide to Protein Purification*, ed. M. Deutscher, vol. 182 of *Methods in Enzymology* (Academic Press, Inc.: San Diego, 1990) and R. Scopes, *Protein Purification: Principles and Practice*, (Springer-Verlag: New York, 1982).

Protein sequence determination

Polypeptide fragments of CsrA are first obtained by digestion with enzymes such as trypsin, clostripain, or Staphylococcus protease or with chemical agents such as cyanogen bromide, O-iodosobenzoate, hydroxylamine or 2-nitro-5-thiocyanobenzoate. Peptide fragments may be separated by reversed-phase HPLC and analyzed by gas-phase sequencing. Peptide fragments are used in order to determine the partial amino acid sequence of a polypeptide by methods known in the art including but not limited to, Edman degradation.

Protein modifications.

The present invention also provides for CsrA polypeptides or fragments thereof which have been modified, by methods including, but not limited to, in vivo or in vitro chemical and biochemical modifications or by the incorporation of unusual amino acids. Such modifications include, for example, acetylation, carboxylation, phosphorylation, glycosylation, ubiguitination, and labeling, e.g., with radionuclides, various enzymatic modifications. There are a variety of standard methods for labeling polypeptides and labels useful for such purposes, including radioactive isotopes such as $^{32}P$, ligands which bind to labeled antiligands (e.g., antibodies) or antiligands which bind to labeled ligands, fluorophores, chemiluminescent agents, and enzymes. See, e.g., *Molecular Cloning: A Laboratory Manual*, 2nd ed., Vol. 1–3, ed. Sambrook, et al., Cold Spring Harbor Laboratory Press (1989); or *Current Protocols in Molecular Biology*, ed. F. Ausubel et al., Greene Publishing and Wiley-Interscience: New York, 1987 and periodic updates.

Polypeptide fragments.

The present invention provides fragments of CsrA polypeptides which retain at least one of the biological activities characteristic of CsrA.

A polypeptide "fragment," "portion," or "segment" is a stretch of amino acid residues of at least about 7–17 amino acids (or the minimum size retaining an antigenic determinant of CsrA and capable of raising CsrA-specific antibodies).

Significant biological activities include the effects on glycogen biosynthesis, gluconeogenesis, cell size, and cell surface properties as described herein. Immunological activities include immunogenic function in a target immune system as well as the capacity to compete for antibody binding to a CsrA epitope.

Fusion polypeptides.

The present invention also provides for fusion polypeptides comprising CsrA polypeptides and fragments thereof. Such fusions may be between two or more CsrA sequences or between the sequences of CsrA and a related or unrelated polypeptide. Such fusion polypeptides may exhibit a combination of properties or activities of the derivative proteins. For immunological purposes, tandemly repeated polypeptide segments may be used as immunogens, thereby producing highly antigenic proteins. Alternatively, such polypeptides may serve as highly efficient competitors for binding. Fusion partners include immunoglobulins, bacterial β-galactosidase, trpE, protein A, β-lactamase, alpha amylase, alcohol dehydrogenase and yeast alpha mating factor. See, e.g., Godowski et al. (1988) *Science* 241:812–816.

Where desired, a signal peptide or leader sequence can be added by recombinant DNA techniques, e.g., to the amino terminus of CsrA, to direct the polypeptide through the membrane of a cell.

Nucleic Acids

A CsrA nucleic acid is one which encodes a CsrA polypeptide. The nucleic acids of the present invention possess a sequence which is either derived from or substantially similar to a natural CsrA-encoding gene, such as the *E. coli* CsrA having the sequence shown in FIG. 9(SEQ ID NO:1).

The DNA compositions of this invention include RNA, cDNA, genomic DNA, synthetic forms, and mixed polymers, both sense and antisense strands, and may be chemically or biochemically modified or contain non-natural or derivatized nucleotide bases. Nucleic acids encoding the CsrA polypeptides of the present invention include not only native or wild-type csrA sequences but also any sequence capable of encoding a CsrA polypeptide, which may be synthesized by making use of the redundancy in the genetic code. Various codon substitutions may be introduced, e.g., silent or conservative changes as discussed above.

One embodiment of the invention is the DNA encoding the csrA gene. The DNA sequence is presented in FIG. 9(SEQ ID NO:1), however, it is to be understood that modifications may be made to the sequence without impairing its ability to encode the CsrA protein. Due to degeneracy in the genetic code there is some degree of flexibility in the third nucleic acid of each codon and some amino acid residues are encoded by several different codons. Each possible codon could be used in the gene to encode the protein. While this may appear to present enumerable choices, in practice, each host has a particular preferred codon usage, so that genes can be tailored for optimal translation in the host in which they are expressed. Thus, synthetic genes that encode the CsrA protein are included in this invention.

The nucleic acids of the present invention may be derived from naturally occurring or recombinant single or double stranded nucleic acids or may be chemically synthesized. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

The present invention also includes homologs of the csrA gene. Typically, homologs are genes encoding homologous proteins such as those found in other species. A polynucleotide or fragment thereof is "substantially homologous" (or "substantially similar") to another if, when optimally aligned (with appropriate nucleotide insertions or deletions) with another polynucleotide (or its complementary strand), there is nucleotide sequence identity in at least about 60% of the nucleotide bases, usually at least about 70%, more usually at least about 80%, preferably at least about 90%, and more preferably at least about 95 to 98% of the nucleotide bases. Homology also exists when a polynucleotide or fragment thereof will hybridize to another under selective hybridization conditions. Kanehisa (1984) *Nuc. Acids Res.* 12:203–213.

The DNA sequences of the present invention comprise at least about 5 codons (15 nucleotides), more usually at least about 7 to 15 codons, and most preferably at least about 35 codons. This number of nucleotides is usually about the minimal length required to hybridize specifically with a CsrA-encoding sequence.

The present invention also includes hybrid genes including CsrA either 5' or 3' of a gene encoding another protein. The fusion of the two genes is such that translation of the hybrid gene results in expression of a fusion protein. Suitable genes for fusion include but are not limited to β-galactosidase, cyclophilin and β-lactamase.

The present invention also includes various genes in which not only the coding sequence of the csrA gene is altered but in which the non-coding regions are altered, deleted or substituted. For instance, a variety of promoters may be used in place of the csrA promoter particularly to optimize expression in a variety of different host cells or to put expression under inducible control. Various suitable promoters are known in the art.

Techniques for nucleic acid manipulation are described generally, for example, in Sambrook et al., 1989 or Ausubel et al., 1987. Reagents useful in applying such techniques, such as restriction enzymes and the like, are widely known in the art and commercially available from vendors including, but not limited to, New England BioLabs, Boehringer Mannheim, Amersham, Promega Biotec, U.S. Biochemicals, New England Nuclear, and a number of other sources.

"Isolated" or "pure"

An "isolated" or "purified" nucleic acid is a nucleic acid, e.g., an RNA, DNA, or a mixed polymer, which is substantially separated from other DNA sequences which naturally accompany a native CsrA sequence, e.g., ribosomes, polymerases, and many other genome sequences. The term embraces a nucleic acid sequence which has been removed from its naturally occurring environment, and includes recombinant or cloned DNA isolates and chemically synthesized analogues or analogues biologically synthesized by heterologous systems.

"Encode"

A nucleic acid is said to "encode" a polypeptide if, in its native state or when manipulated by methods known to those skilled in the art, it can be transcribed and/or translated to produce the polypeptide of a fragment thereof. The anti-sense strand of such a nucleic acid is also said to encode the sequence.

"Operably linked"

A nucleic acid sequence is operably linked when it is placed into a functional relationship with another nucleic acid sequence. For instance, a promoter is operably linked to a coding sequence if the promoter affects its transcription or expression. Generally, operably linked means that the DNA sequences being linked are contiguous and, where necessary to join two protein coding regions, contiguous and in reading frame.

"Recombinant"

A "recombinant" nucleic acid is one which is chemically synthesized or the product of the artificial manipulation of isolated segments of nucleic acids, e.g., by genetic engineering techniques.

Probes, primers, and antisense nucleic acids

Nucleic acid probes and primers based on csrA sequences may be prepared by standard techniques. Such a probe or primer comprises an isolated nucleic acid. In the case of probes, the nucleic acid further comprises a label (e.g., a radionuclide such as $^{32}P$ or $^{35}S$) or a reporter molecule (e.g., a ligand such as biotin or an enzyme such as horseradish peroxidase). Probes may be used to identify the presence of a hybridizing nucleic acid sequence, e.g., a csrA mRNA in a sample or a cDNA or genomic clone in a library. Primers may be used, for example, for amplification of nucleic acid sequences, e.g., by the polymerase chain reaction (PCR). See, e.g., *PCR Protocols: A Guide to Methods and Applications*, Innis, M., et al., eds., Academic Press: San Diego (1990). The preparation and use of probes and primers is described, e.g., in Sambrook et al. (1989) or Ausubel et al. (1987).

Antisense nucleic acids capable of specifically binding to CsrA sequences are also useful for interfering with CsrA gene expression. See, e.g., EPO publication 431523A2.

Preparation of recombinant or chemically synthesized nucleic acids; vectors, transformation, host cells Another embodiment of the present invention encompasses DNA expression systems containing the CsrA gene. A wide variety of suitable expression systems are known in the art and are selected based on the host cells used, inducibility of expression desired and ease of use. Expression systems are defined as polynucleotides which, when transformed into an appropriate host cell, can express a protein(s). The polynucleotides possess a nucleotide sequence which is substantially similar to a natural protein-encoding polynuoleotide or a fragment thereof.

The nucleic acids of the present invention may be produced in large amounts by replication of a suitable recombinant vector comprising CsrA sequences in a compatible host cell. Alternatively, these nucleic acids may be chemically synthesized, e.g., by any method known in the art, including, but not limited to, the phosphoramidite method described by Beaucage and Carruthers (1981) *Tetra. Letts.* 22:1859–1862 and the triester method according to Matteucci et al. (1981) *J. Am. Chem. Soc.* 103:3185, preferably using commercial automated synthesizers.

The purification of nucleic acids produced by the methods of the present invention is known in the art and includes, but is not limited to, those described, e.g., in Sambrook et al. (1989) or Ausubel et al. (1987).

DNA constructs prepared for introduction into a prokaryotic or eukaryotic host typically comprise a replication system recognized by the host, including the intended DNA fragment encoding the desired polypeptide, and preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals from secreted polypeptides may also be included to allow the polypeptide to cross and/or lodge in cell membranes or be secreted from the cell. Such vectors may be prepared by means of standard recombinant techniques discussed, for example, in Sambrook et al. (1989) or Ausubel et al. (1987).

An appropriate promoter and other necessary vector sequences is selected so as to be functional in the host, and may, when appropriate, include those naturally associated with csrA genes. Examples of workable combinations of cell lines and expression vectors are described in Sambrook et al. (1989) or Ausubel et al. (1987); see also, e.g., Metzger et al. (1988) *Nature* 334:31–36. Many useful vectors are known in the art and may be obtained from vendors including, but not limited to, Stratagene, New England Biolabs, Promega Biotech, and others. Promoters including, but not limited to, the trp, lac and phage promoters, tRNA promoters and glycolytic enzyme promoters may be used in prokaryotic hosts. Useful yeast promoters include, but are not limited to, the promoter regions for metallothionein, 3-phosphoglycerate kinase or other glycolytic enzymes such as enolase or glyceraldehyde-3-phosphate dehydrogenase, enzymes responsible for maltose and galactose utilization. Suitable vectors and promoters for use in yeast expression are further described in Hitzeman et al. EP 73,657A. Appropriate foreign mammalian promoters include, but are not limited to, the early and late promoters from SV40 (Fiers et al. (1978) *Nature* 273:113) and promoters derived from murine Molony leukemia virus, mouse mammary tumor virus, avian sarcoma viruses, adenovirus II, bovine papilloma virus or polyoma. In addition, the construct may be joined to an amplifiable gene (e.g., DHFR) so that multiple copies of the construct may be made. For appropriate enhancer and other expression control sequences see also *Enhancers and Eukaryotic Gene Expression*, Cold Spring Harbor Press: N.Y., 1983.

While such expression vectors are preferably autonomously replicating, they may also be inserted into the genome of the host cell by methods known in the art.

Expression and cloning vectors preferably contain a selectable marker which is a gene encoding a protein necessary for the survival or growth of a host cell transformed with the vector. The presence of this gene ensures the growth of only those host cells which express the inserts. Typical selection genes are known in the art and include, but are not limited to, those which encode proteins that (a) confer resistance to antibiotics or other toxic substances, e.g. ampicillin, neomycin, methotrexate, etc.; (b) complement auxotrophic deficiencies, or (c) supply critical nutrients not available from complex media, e.g. the gene encoding D-alanine racemase for Bacilli. The choice of the proper selectable marker depends on the host cell, and appropriate markers for different hosts are well known.

The nucleic acids of the present invention can be introduced into host cells by any method known in the art, which vary depending on the type of cellular host, including, but not limited to, electroporation; transfection employing calcium chloride, rubidium chloride calcium phosphate, DEAE-dextran, or other substances; microprojectile bombardment; lipofection; infection (where the vector is an infectious agent, such as a retroviral genome); and other methods. See generally, Sambrook et al. (1989) and Ausubel et al. (1987). The cells into which these nucleic acids have been introduced also include the progeny of such cells.

While prokaryotic host cells are preferred, mammalian or other eukaryotic host cells, including, but not limited to, yeast, filamentous fungi, plant, insect, amphibian or avian species, may also be useful for production of the proteins of the present invention. See, *Tissue Culture*, Kruse and Patterson, ed., Academic Press (1973). Examples of commonly used mammalian host cell lines are VERO and HeLa cells, Chinese hamster ovary (CHO) cells, and WI38, BHK, and COS cell lines, or others as appropriate, e.g., to provide higher expression, desirable glycosylation patterns, etc.

Another embodiment of the present invention is a method of altering metabolic pathways controlled by csrA. Such pathways include but are not limited to glycogen biosynthesis and gluconeogenesis. Such methods are useful for directly increasing or decreasing expression of genes that are directly under csrA control and for indirectly enhancing production of products via pathways that are not under csrA control. Such products include, but are not limited to, antibiotics, acetic acid, amino acids, organic acids, alcohols, and a wide variety of other industrially important compounds produced in bacterial fermentation systems. The suitable methods of altering the expression of csrA are known in the art and include, but are not limited to, the methods described herein.

Antibodies

The present invention also provides polyclonal and/or monoclonal antibodies capable of specifically binding to the CsrA polypeptides and fragments thereof, produced by standard in vitro or in vivo techniques. Such antibodies are raised against a CsrA polypeptide and are capable of distinguishing CsrA antibodies from other polypeptides.

For production of polyclonal antibodies, an appropriate host animal is selected, typically a mouse or rabbit. The substantially purified antigen, whether the whole CsrA polypeptide, a fragment thereof, or a CsrA polypeptide coupled or fused to another polypeptide, is presented to the immune system of the host by methods appropriate for the host, commonly by injection into the footpads, intramuscularly, intraperitoneally, or intradermally. Peptide fragments suitable for raising antibodies may be prepared by chemical synthesis, and are commonly coupled to a carrier molecule (e.g., keyhole limpet hemocyanin) and injected into a host over a period of time suitable for the production of antibodies. The sera is tested for immunoreactivity to the CsrA protein or fragment. Monoclonal antibodies may be made by injecting the host with the protein polypeptides, fusion proteins or fragments thereof and following methods known in the art for production of such antibodies. See, E. Harlow and D. Lane (1988) *Antibodies: A Laboratory Manual*, CSH Laboratories.

An immunological response is usually assayed with an immunoassay, a variety of which are provided, e.g., in Harlow and Lane (1988) *Antibodies: A Laboratory Manual*, CSH Laboratories; or Goding (1986) *Monoclonal Antibodies: Principles and Practice*, 2d ed, Academic Press, New York, although any method known in the art can be used.

Monoclonal antibodies with affinities of $10^8$ $M^{-1}$ preferably $10^9$ to $10^{10}$, or stronger are typically made by standard procedures as described, e.g., in Harlow and Lane (1988) or Goding (1986). Briefly, appropriate animals are immunized with the antigen by a standard protocol. After the appropriate period of time, the spleens of such animals are excised and individual spleen cells fused, typically, to immortalized myeloma cells under appropriate selection conditions. Thereafter the cells are clonally separated and the supernatants of each clone are tested for their production of an appropriate antibody specific for the desired region of the antigen.

Other suitable techniques of antibody production include, but are not limited to, in vitro exposure of lymphocytes to the antigenic polypeptides or selection of libraries of antibodies in phage or similar vectors. See Huse et al. (1989) *Science* 246:1275-1281.

Frequently, the polypeptides and antibodies are labeled, either covalently or noncovalently, with a substance which provides for a detectable signal. A wide variety of labels and conjugation techniques are known. Suitable labels include, but are not limited to, radionuclides, enzymes, substrates, cofactors, inhibitors, fluorescent agents, chemiluminescent agents, magnetic particles. Patents, teaching the use of such labels include, but are not limited to, U.S. Pat. Nos. 3,817,837; 3,850,752; 3,939,350; 3,996,345; 4,277,437; 4,275,149; and 4,366,241. Also, recombinant immunoglobulins may be produced by any method known in the art. See Cabilly, U.S. Pat. No. 4,816,567.

The invention will be better understood by reference to the following examples, which are intended to merely illustrate but not limit the best mode now known for practicing the invention.

EXAMPLE 1

Genetic and physical mapping of the regulatory gene csrA on the *Escherichia coli* K-12 chromosome The chromosomal location of the TR1-5 mutation in csrA was first mapped with a set of seven Hfr strains by the method described by Singer et al. (1989) *Microbiol. Rev.* 53:1–24. Each of the Hfr strains transfers a tetracycline resistance (Tet$^r$) marker approximately 20 minutes after mating is initiated. The recipient strain, TR1-5[pCZ3-3] (see Table 1 below), was tetracycline sensitive (Tet$^s$) and ampicillin resistant (Amp$^r$) and produced elevated levels of glycogen. Transconjugants were selected on ampicillin (100 µg/ml) and scored for glycogen biosynthesis by staining colonies with iodine vapor, as described by Romeo et al. (1988). Only conjugation with Hfr 5 of the set, CAG5055 (P045 relA1 thi-1 zed-3069::TN10), produced transconjugants with the low-glycogen (wild-type) phenotype of the Hfr parent (36 low-glycogen colonies of a total of 57 colonies), indicating that the mutation that affects glycogen synthesis resides between 43 and 62 minutes.

Transductional mapping of the TR1-5 mutation was conducted to determine its distance from 20 individual Tet$^r$ markers spanning the 43- to 62-minute region in a collection of Tet mapping strains according to the method described by Singer et al. (1989). A P1vir lysate from TR1-5 was used to transduce the Kan$^r$ marker into each of the 20 mapping strains. The Kan$^r$ (resistant to 100 µg of kanamycin per ml), high-glycogen transductants were picked and tested for Tet$^r$. Only 2 of the 20 mapping strains yielded Tet$^r$ transductants; CAG18642 (zfh-3131::Tn10, 57.5 minutes) yielded 6 of 9 Tet$^r$ transductants and CAG12173 (cysC95::Tn10, 59.25 minutes) yielded 2 of 10 Tet$^r$, indicating that the csrA gene maps clockwise from 57.5 minutes. To map csrA more precisely, a P1vir lysate of TR1-5 CAG18642 (a Tet$^r$ Kan$^r$ high-glycogen transductant) was used to transduce CAG12033 (Tet$^r$ Kan$^s$) to tetracycline resistance, and the transductants were screened for the high-glycogen phenotype. Selection on tetracycline gave 51 high-glycogen transductants of a total of 91 transductants, indicating that csrA maps to 58 minutes. Wu (1966) *Genetics* 54:405–410. The latter cross also allowed the linkage of the Kan$^r$ marker with the glycogen phenotype to be evaluated. All 30 of the high-glycogen transductants tested were Kan$^r$ and all 25 of the low-glycogen transductants tested were Kan$^s$, supporting the conclusion that the high-glycogen phenotype was caused by the insertion of the Kan$^r$ marker at 58 minutes.

The physical location of csrA was determined by hybridization. Cloning of the Kan$^r$ marker and some flanking chromosomal DNA from a TR1-5 secondary transductant into pUC19, to generate pTR151, is described below. A 1.7-kb EcoRI-PstI fragment from the chromosomal insert DNA of pTR151 was excised, purified on low-melting-point agarose, and used as a template to synthesize a $^{32}$P-labeled probe, using random-primed DNA synthesis according to the method described by Feinberg and Vogelstein (1983) *Anal. Biochem.* 132:6–13 (Addendum, 137:266–267). The probe was hybridized to DNA of a commercially available miniset of the Kohara collection of *E. coli* K-12 genome according to the manufacturer's specifications. Takara Biochemical, Berkeley, Calif.; Kohara et al. (1987) Cell 50:495–508. The probe hybridized specifically with only one clone of the miniset, λ446. This phage contains DNA from approximately 2825 to 2847 kb on the chromosome. This physical location is consistent with the transductional mapping data. The CsrA gene, identified by the TR1-5 Kan$^r$ marker, lies at approximately 2830 kb of the original Kohara map (Kohara et al. (1987)) or at 2834.8 kb on a revised map of *E. coli* K-12 gene sequences compiled with a computer. Rudd et al. (1991). The csrA gene has now been found to be located within a 0.7-kb region that separates the previously sequenced genes alas and serV. Putney et al. (1981); and Komine et al. (1990).

EXAMPLE 2

Isolation of a transposon mutant, TR1-5, that exhibits altered expression of the glycogen biosynthesis genes Table 1 lists the strains, plasmids, and bacteriophages that were used in the examples described below and their sources and relevant genotypes. Cultures were grown in either Kornberg medium (containing 0.5% glucose according to the method described by Romeo and Preiss (1989) LB medium (pH 7.4) according to the method described by Miller (1972) *Experiments in Molecular Genetics*, Cold Spring Harbor Laboratories, Cold Spring Harbor, N.Y., LB-glucose (LB containing 0.2% glucose), M9 medium (0.5% carbon source, Miller (1972)), or supplemented morpholinepropane sulfonic acid (MOPS) medium according to the method described by Wanner et al. (1977) *J. Bacteriol.* 130:212–222. Liquid cultures were grown with rapid gyratory shaking at 37° C. or as otherwise indicated. Cultures were inoculated with one volume of an overnight culture per 100 volumes of fresh medium or as otherwise indicated. Solid media contained 1.5% agar. Solid Kornberg medium for detection of endogenous glycogen contained 1% glucose. Anaerobic conditions for solid and liquid cultures were maintained by using a BBL GasPak system (Beckton Dickinson, Cockeysville, Md.). Antibiotics were used at the following concentrations: ampicillin, 100 μg/ml; tetracycline, 10 μg/ml; kanamycin, 100 μg/ml; and chloramphenicol, 10 μg/ml.

To identify the genes that regulate the expression of the glg genes, BW3414(pCZ3-3) was mutagenized with a mini-kanR element according to the method described by Way et al. (1984) *Gene* 31:369–379. This strain lacks a chromosomal copy of lacZ but contains native chromosomally encoded copies of the glg genes, as well as a plasmid-encoded glgC'-'lacZ translational fusion. The expression of this glgC'-'lacZ fusion is controlled by all of the factors that are known to regulate the native glgC gene. Romeo et al. (1990) *Curr. Microbiol.* 21:131–137.

Transposon mutants were constructed by infecting BW3414 (pCZ3-3) with λNK1298 with a multiplicity of infection of 0.025 according to the method described by Way et al. (1984). Cells were plated onto Kornberg medium containing effective amounts of kanamycin and ampicillin, the plates were incubated overnight at 37° C., and glycogen synthesis mutants were identified by staining with iodine vapor according to the method described by Romeo et al. (1988). β-galactosidase activities in mutants which exhibited either increased or decreased iodine staining were determined. Approximately 15,000 Kan$^r$ mutants were generated, and β-galactosidase activity was determined for 47 glycogen mutants. TR1-5 mutant exhibited intense iodine staining and five- to six-fold higher β-galactosidase activity than the parent strain, although four other glycogen excess, glgC'-'lacZ-overexpressing mutants which showed less dramatic effects were isolated. The transposon which was used was expected to generate stable mutations. Way et al. (1984). The TR1-5 mutant was found to be phenotypically stable during extensive growth experiments, indicating that second-site reversions do not present a problem in handling this strain.

TABLE 1

Bacterial strains, bacteriophages, and plasmids used in the Examples

| Strain, phage, or plasmid | Description | Source and/or reference |
|---|---|---|
| *E. coli* K-12 | | |
| BW3414 | ΔlacU169 | Barry Wanner |
| CAG18642 | zfh-3131::Tn10; 57.5 min | Singer, et al. (1989) |
| CF1648 | [MG1655] (prototrophic) | Xiao, et al. (1991) J. Biol. Chem. 266:5980–5990 |
| CF1651 | ΔrelA in CF1648 | Xiao, et al. (1991) |
| CF1693 | ΔspoT in CF1651 | Xiao, et al. (1991) |
| G6MD3 | Hfr his thi Str$^S$ Δ(malA-asd) | Schwartz (1966) J. Bacteriol. 92:1083–1089 |
| HG137 | pck-13::Mu dl pps ΔlacU169 | Goldie (1984) J. Bacteriol. 159:832–836 |
| HB101 | supE44 hsdS20 (r$_B^-$m$_B^-$) recA13 ara-14 proA2 lacY1 galK2 rpsL20 xyl-5 mtl-1 | Boyer and Roulland-Dussoix (1969) J. Mol. Biol. 41:459–472 |
| LE392 | hsd R514 (r$_K^-$m$_K^-$) supE44 supF58 lacY galK2 galT22 metB1 trpR55λ- | Donna Daniels and Fred Blattner |
| ML2 | met gal hsdK$_R$ supE supF Km$^r$ Δcya | Guerinot and Chelm (1984) J. Bacteriol. 159:1068–1071 |
| NK5012 | supE44 hsdR thi-1 thr-1 leuB6 lacY1 ton A22 trp tonA21 Φ80$^r$15$^r$ | Nancy Kleckner |
| SA2777 | F$^-$ rpsL relA Δcrp::Cm$^r$ | S. Garges and S. Adhya |
| TR1-5* | csrA::kan$^r$ | This study, |
| ZK916 | W3110 ΔlacU169 tna-2 λMAV103 (bolA::lacZ) | Bohannan, et al. (1991) |
| *E. coli* B | | |
| AC70R1 | glgQ | Jack Preiss |
| Bacteriophages | | |
| λNK1298 | Tn10-mini Kan$^r$ hopper | N. Kleckner |
| λ446 | Clone (csrA$^+$) from the Kohara collection | Kohara, et al. (1987) |
| P1vir | Strictly lytic P1; forms clear plaques | Miller (1972) |
| Plasmids | | |
| pUC19 | Cloning vector; high copy number | Yanish-Perron, et al. (1985) Gene 33:103–119 |

TABLE 1-continued

Bacterial strains, bacteriophages, and plasmids used in the Examples

| Strain, phage, or plasmid | Description | Source and/or reference |
|---|---|---|
| pLG339 | Cloning vector; low copy number | Stoker, et al. (1982) Gene 18:335-341 |
| pOP12 | Contains asd and glg gene cluster in pBR322 | Okita, et al. (1981) J. Biol. Chem. 256:6944-6952 |
| pMLB1034 | For construction of 'lacZ translational fusions | Silhavy, et al. (1984) |
| pCZ3-3 | ΦglgC'-'lacZ in pMLB1034 | Romeo and Priess (1990) |
| pBZ1 | ΦglgB'-'lacZ in pMLB1034 | This study |
| pCSR10 | csrA gene, 0.5-kb DdeI from λ446 in pUC19 | This study |
| pCSR-L1 | pCSR10 deletion | This study |
| pCSR-D3 | pCSR10 deletion | This study |
| pCSR-D1-D | pCSR10 deletion | This study |
| pCSR-D1-L | pCSR10 deletion | This study |
| pTR151 | Clone of TR1-5 (csrA::kan$^r$) in pUC19 | This study |
| pLEP2-2 | Part of serV operon from λ446 in pUC19 | This study |
| pPV1 | Part of serV operon from λ446 in pUC19 | This study |
| DW18 and RH105 | | Hengge-Aronis et al., Molec. Microbiol. (1992) 6:1877-1886 |

An a strain designation containing the prefix TR1-5 indicates that the wild-type (csrA+) allele has been replaced by the TR1-5 mutant allele (CsrA::kan$^r$) by P1vir transduction.

EXAMPLE 3

The TR1-5 mutation alters glycogen biosynthesis via effects on the expression of two glycogen biosynthetic operons

The extremely intense staining of colonies of the TR1-5 mutant indicated that glycogen levels were much higher than in the parent strain. The TR1-5 mutation was transduced into BW3414 to generate a mutant strain that did not carry the pCZ3-3 plasmid and to provide a genetic background which had not been subjected to transposon mutagenesis. Transduction of the TR1-5 (CsrA::kanR) mutation was conducted by using P1vir according to the method described by Miller (1972). Transductants were isolated either by direct selection for the Kan$^r$ phenotype or by cotransduction of the closely linked Tet$^r$ marker in TR1-5CAG18642. Romeo and Gong (1993).

Glycogen levels were quantitatively determined in the mutant TR1-5BW3414 and wild-type BW3414 strains and were compared. Cultures were grown in Kornberg medium and were harvested in early (6 h) or late (24 h) stationary phase. The results presented in Table 2 indicate that TR1-5BW3414 accumulated 20- to 30-fold more glycogen than the parent strain, consistent with the qualitative results of iodine staining.

TABLE 2

Glycogen and ADPglucose pyrophosphorylase levels and E. coli K-12 BW3414 (csrA+) and TR1-5BW3414 (csrA::kanR)

| | ADPglucose pyrophosphorylase (U/mg of protein ± SD) | | Glycogen (mg/mg of protein ± SD) | |
|---|---|---|---|---|
| Strain | Exponential growth phase | Stationary growth phase | Early stationary phase | Late stationary phase |
| BW3414 | 0.08 ± 0.00 | 0.23 ± 0.01 | 0.06 ± 0.01 | 0.012 ± 0.001 |
| TR1-5BW3414 | 0.25 ± 0.01 | 2.15 ± 0.50 | 1.61 ± 0.07 | 0.346 ± 0.003 |

ADP glucose pyrophosphorylase activity in the pyrophosphorolysis direction, the amount of total cellular protein, and β-galactosidase activity were determined as previously described by Romeo et al. (1990); and Romeo et al. (1991).

Briefly, for ADPglucose pyrophosphorylase activity, cultures were grown in Kornberg medium from a 1:400 inoculum and were harvested in late-exponential (7 h) or stationary (24 h) phase. One unit of activity is defined as 1 μmol of product formed per 10 minutes, in the pyrophosphorolysis direction, under maximal allosteric activation.

The β-galactosidase activity was normalized with respect to protein instead of culture turbidity, since it was found that the turbidity ($A_{600}$) of the TR1-5 mutant in liquid culture was significantly higher than that of the parent strain in the early stationary phase for equivalent levels of cellular protein. Each of the growth curve experiments was conducted at least twice to ensure that results attributed to strain differences were reproducible. Glycogen was isolated and enzymatically quantified according to the method described by Preiss et al. (1976).

Enzymes for assaying glycogen were purchased from Sigma Chemical Co. (St. Louis, Mo.) (hexokinase and glucose-6-phosphate dehydrogenase) or from Boehringer Mannheim Biochemicals (Indianapolis, Ind.) (α-amylase and amyloglucosidase).

Levels of ADPglucose pyrophosphorylase were found to be significantly higher in the TR1-5 mutant than in an isogenic wild-type strain, in both the exponential and stationary phases of growth, with the maximal difference of almost 10-fold occurring in the stationary phase (Table 2). The specific activity of β-galactosidase expressed from the glgC'-'lacZ fusion was monitored throughout the exponential and stationary phases of wild-type and TR1-5 mutant strains. The TR1-5 mutant overexpressed this gene fusion in both the exponential and stationary phases (FIG. 1). It was observed that specific β-galactosidase activity was sevenfold higher in stationary phase (24 h) versus mid-log phase in both mutant and wild-type strains and that a change of approximately two- to three-fold in activity occurred after the cultures had already entered stationary phase.

Figure 2:
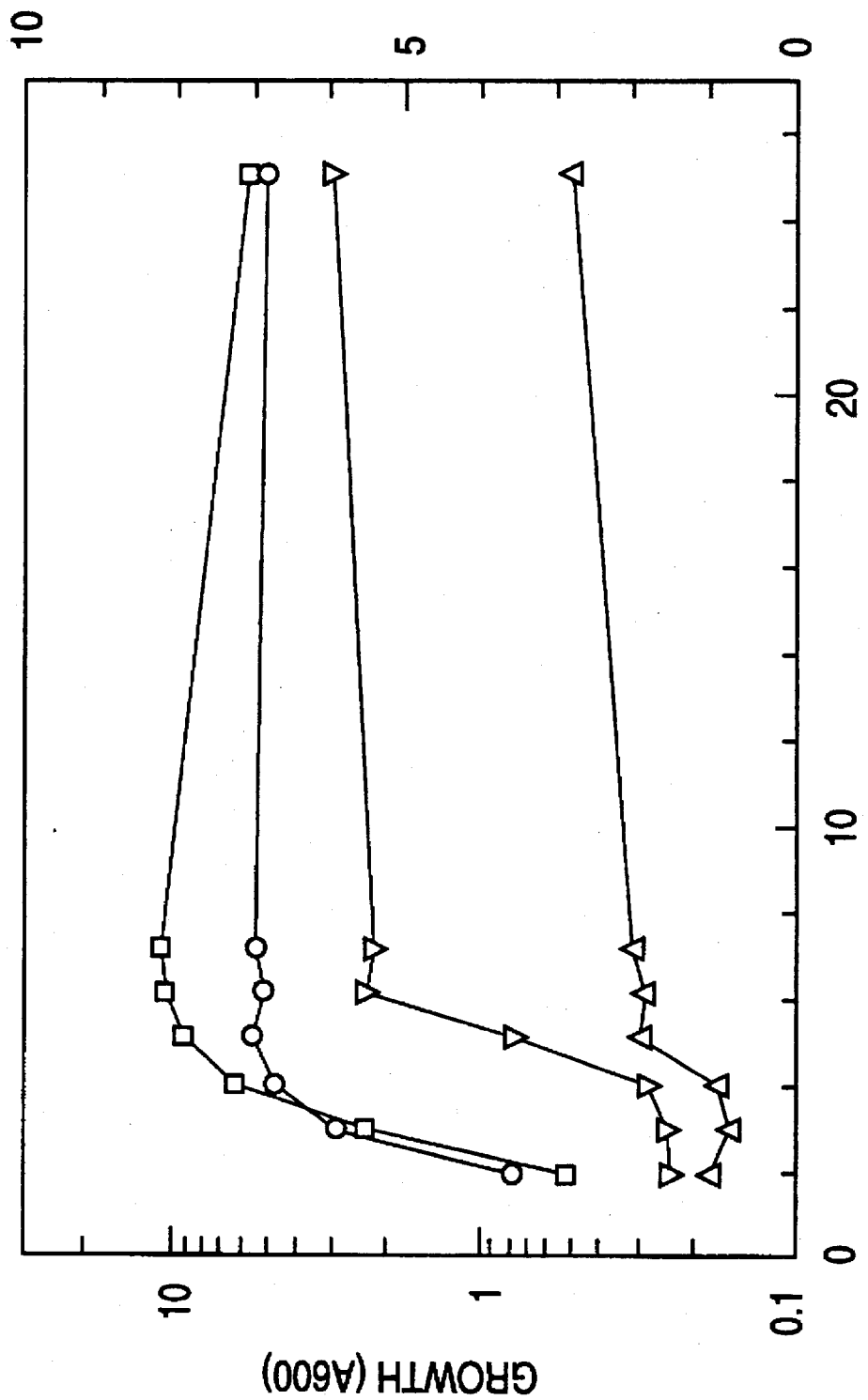
FIG. 2 is a graph depicting levels of expression of a glgB'-'lacZ fusion in BW3414 and TR1-5BW3414. Sample identities are as described in the legend to FIG. 2, except that the strains contained plasmid pBZ1 instead of pCZ3-3.

In addition to the glgCA genes, glycogen biosynthesis depends on glgB expression to provide the glycogen branching enzyme, which catalyzes the formation of the α-1,6 branches of glycogen. A glgB'-'lacZ translational fusion was constructed to allow glgB expression to be readily determined. A 0.34-kb BamHI-HindI fragment of pOP12 that spans the region from +53 bp of the glgB coding region upstream through the 275-bp glgB-asd intervening region and 8 bp into the coding region of asd was cloned into the BamHI-SmaI cloning site of pMLB1034. Baecker et al. (1986); Haziza et al. (1982) *EMBO J.* 1:379-384; and Silhavy et al. (1984) *Experiments with Gene Fusions*, Cold Spring Harbor Laboratory, Cold Spring Harbor, N.Y. The resulting plasmid, pBZ1, contained an in-frame translational fusion of codon 18 of glgB with codon 7 of lacZ. The specific β-galactosidase activity that was expressed from this glgB'-'lacZ fusion was two- to three-fold higher in the TR1-5 mutant than in the isogenic wild-type strain (FIG. 2). The induction of the glgB'-'lacZ-encoded β-galactosidase activity in the mutant occurred at the same time in the growth curve and with a similar degree of stationary-phase activation, approximately 3.5- to 4-fold, as observed in the wild-type strain, i.e., the shapes of the induction curves were similar.

EXAMPLE 4

Figure 3A:
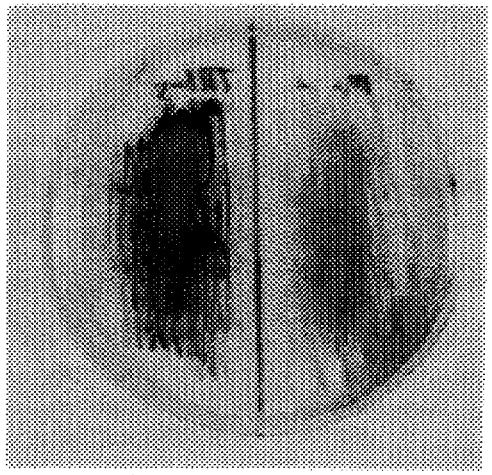
FIG. 3 shows the growth patterns of various cell lines on solid growth medium. The growth patterns show the effects of the TR1-5 mutation on glycogen biosynthesis in cAMP (Δcya) or cAMP receptor protein (crp)-deficient strains. The TR1-5 mutation was introduced by P1vir transduction into strains that lack cAMP (Δcya) or a functional cAMP receptor protein (crp).
Figure 3B:
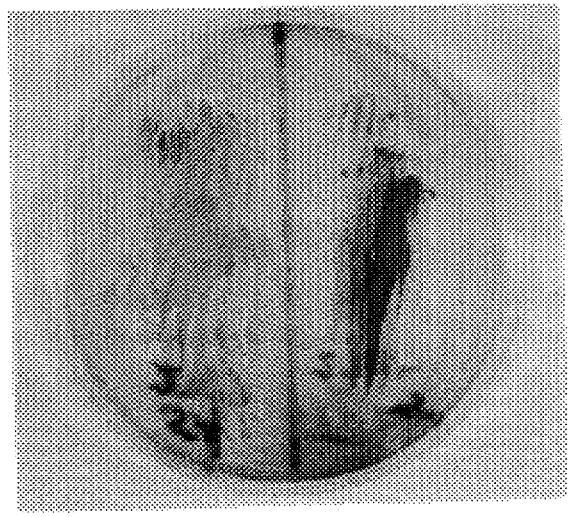
Figure 4:
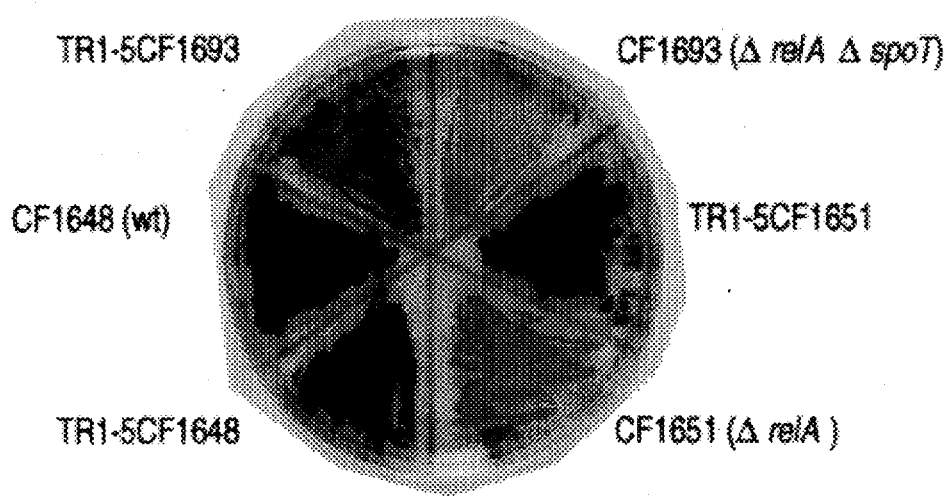
FIG. 4 shows the growth patterns of various cell lines on solid growth medium. The growth patterns show the effects of the TR1-5 mutation on glycogen synthesis in strains deficient in ppGpp. The TR1-5 mutation was introduced by P1 transduction into strains that are either prototrophic, deficient in ppGpp (ΔrelA), or completely lack ppGpp (ΔrelA ΔspoT).

The TR1-5 mutation affects glycogen biosynthesis independently of cAMP and ppGpp The observation that glgB expression was elevated in the TR1-5 mutant indicated that its effect on glycogen levels was not mediated indirectly via cAMP or ppGpp, which have been shown not to regulate glgB. Romeo et al. (1990) and Romeo and Preiss (1989). To directly test this idea, the TR1-5 mutation was transduced into several strains that were deficient in one or more of the genes needed for cAMP or ppGpp control. Cultures were incubated overnight on Kornberg medium and stained for endogenous glycogen with iodine vapor. The TR1-5 mutation resulted in enhanced glycogen levels in cAMP-deficient (Δcya) and in cAMP receptor protein-deficient (crp) strains (FIG. 3) and in strains that accumulate low levels of ppGpp (ΔrelA) or are completely deficient in ppGpp (ΔrelAΔspoT; FIG. 4). These results showed that the TR1-5 mutation affects glycogen biosynthesis independently of the factors that were previously known to regulate the expression of glgCA.

EXAMPLE 5

Expression of a pckA-lacZ transcriptional fusion is enhanced in TR1-5

Figure 5:
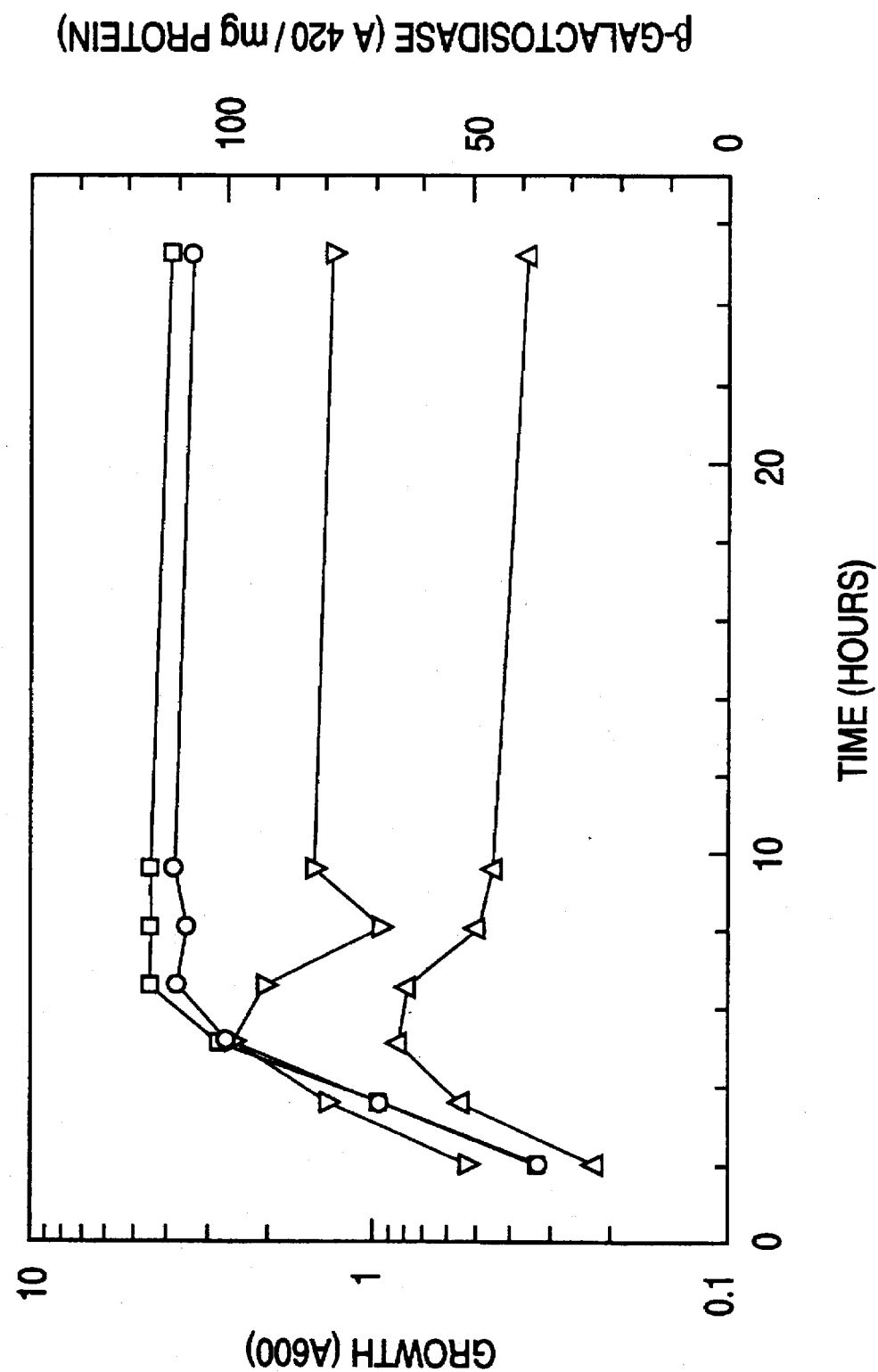
FIG. 5 is a graph depicting levels of expression of a chromosomally encoded pckA::lacZ transcriptional fusion in HG137 and TR1-5HG137. Sample identities are as indicated in the legend to FIG. 2, except that the genetic background was HG137 instead of BW3414.

To test whether the TR1-5 mutation affects the expression of genes in other metabolic systems, the pathway for gluconeogenesis was examined. Gluconeogenesis is functionally related to glycogen synthesis, since it can provide glucose-1-phosphate for glycogen biosynthesis and for other biosynthetic processes when exogenous glucose is not available for cell growth. The expression of pckA, the gene encoding a key regulatory enzyme for gluconeogenesis, phosphoenolpyruvate carboxykinase (EC 4.1.1.49), has been shown to be subject to growth phase control and to positive regulation by cAMP. Goldie (1984). The TR1-5 mutation was transduced into HG137, a strain containing a chromosomally encoded pckA-lacZ operon fusion. Goldie (1984). Cultures were grown in LB medium without added glucose, at 32° C. The specific β-galactosidase activity from this gene fusion was twofold higher in the TR1-5 mutant that in the isogenic wild-type parent. The induction curve in the mutant paralleled that of the wild-type strain (FIG. 5).

EXAMPLE 6

Effects of the TR1-5 mutation on cell morphology

Figure 6A:
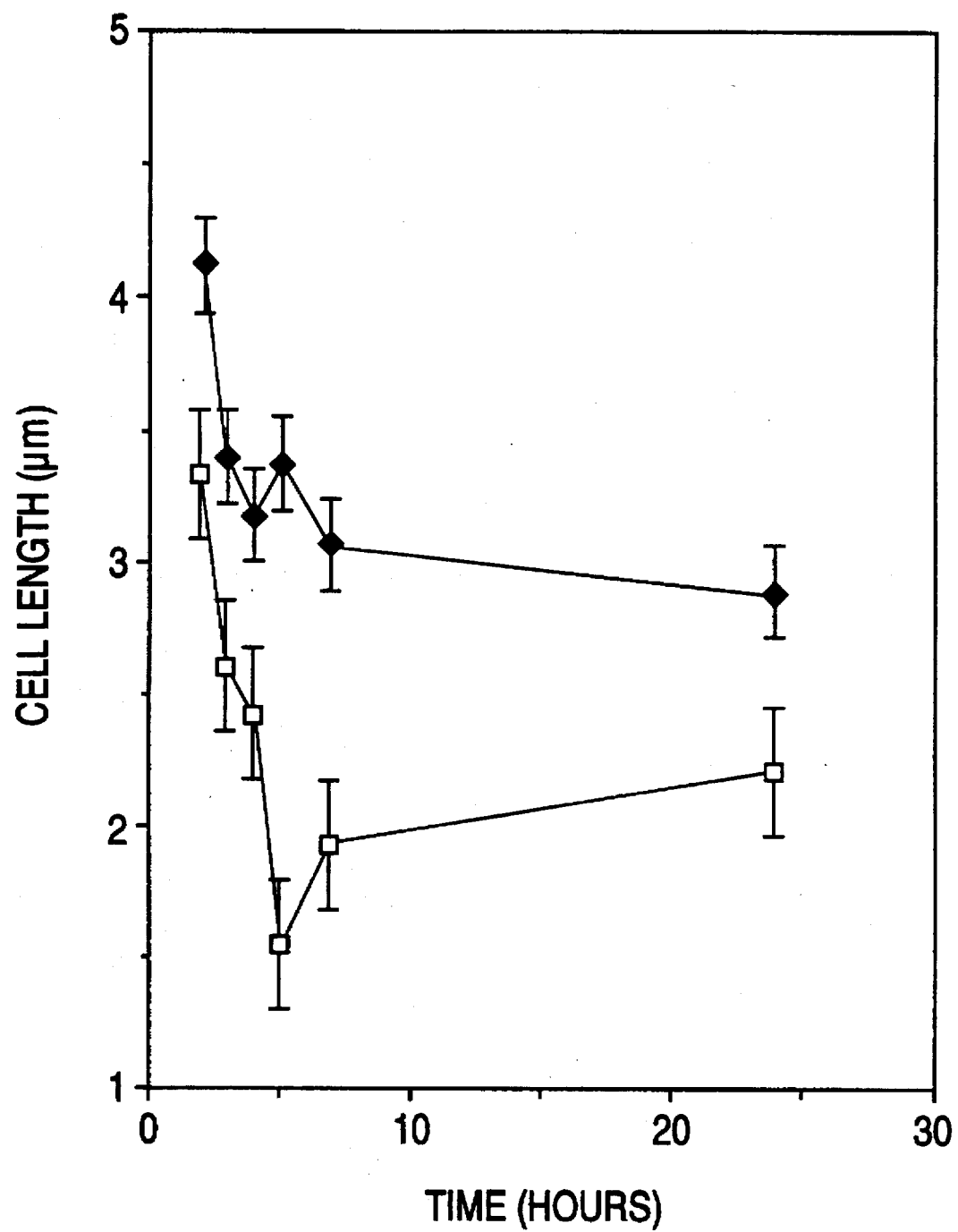
FIGS. 6A and 6B are graphs depicting the effects of TR1-5 mutation on cell size. (A) Cell length as determined by electron microscopy. Strain BW3414 is shown as open squares; TR1-5BW3414 is shown as filled diamonds. (B) Comparison of viable counts versus cellular protein. Viable counts for BW3414 and TR1-5BW3414 are shown as circles and squares, respectively, and protein for these strains is shown as triangles with apices facing up or down, respectively.
Figure 6B:
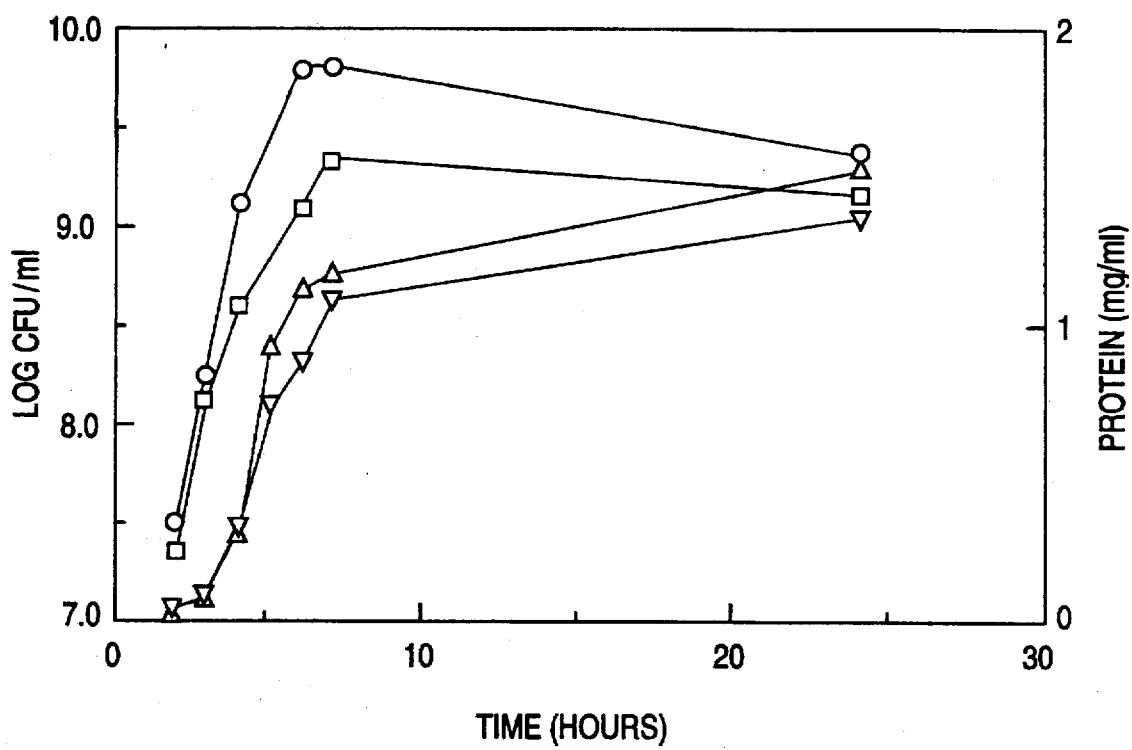

It was observed that the maximum turbidity of liquid cultures of strains containing the TR1-5 mutation was higher than that of isogenic wild-type strains in Kornberg medium (FIGS. 1, 2, and 6). Although it is possible that the high level of glycogen present in the mutant cells may affect turbidity, the size of individual cells was considered to be another parameter that might account for this result. The sizes of mutant and wild-type cells were compared both by direct measurements of cell length taken from electron micrographs and by calculation of viable counts per milligram of protein.

A rapid method for preparing cells for transmission electron microscopy which did not require sectioning was developed. Cells were washed, and the cell density was adjusted to approximately $5 \times 10^9$ cells per ml in 0.06M potassium phosphate buffer, pH 6.8. One drop (10 µl) of this suspension was transferred to a 150-mesh grid that had been coated with Formvar and carbon and then glow discharged. After one minute, the excess buffer was removed and a drop of 4% glutaraldehyde in the same buffer was placed on the grid for 10 minutes, followed by postfixation with 2% osmium tetroxide for 10 minutes. The grid was rinsed three times on drops of distilled water and transferred to a drop of methylcellulose containing 0.2% uranyl acetate for 10 minutes. The grid was removed from this suspension with a 3.5-mm-diameter NiCr loop, excess methylcellulose was removed with filter paper, and the grid was allowed to dry for 10 minutes. The grid was removed from the loop with a thin needle. Micrographs of cells were taken at a magnification of ×5,000 with a Hitachi 600 transmission electron microscope.

The ratio of CFU per milligram of protein for the wild type versus the isogenic TR1-5 mutant indicated that the mutant strain was 1.74-, 2.55-, 3.36-, 4.05-, 4.12-, and 1.42-fold larger at 2, 3, 4, 6, 7, and 24 h, respectively. Therefore, the maximal difference in size occurred in early stationary phase; this was apparently because cells of the mutant strain did not undergo a dramatic decrease in size during entry into the stationary phase.

Figure 7:
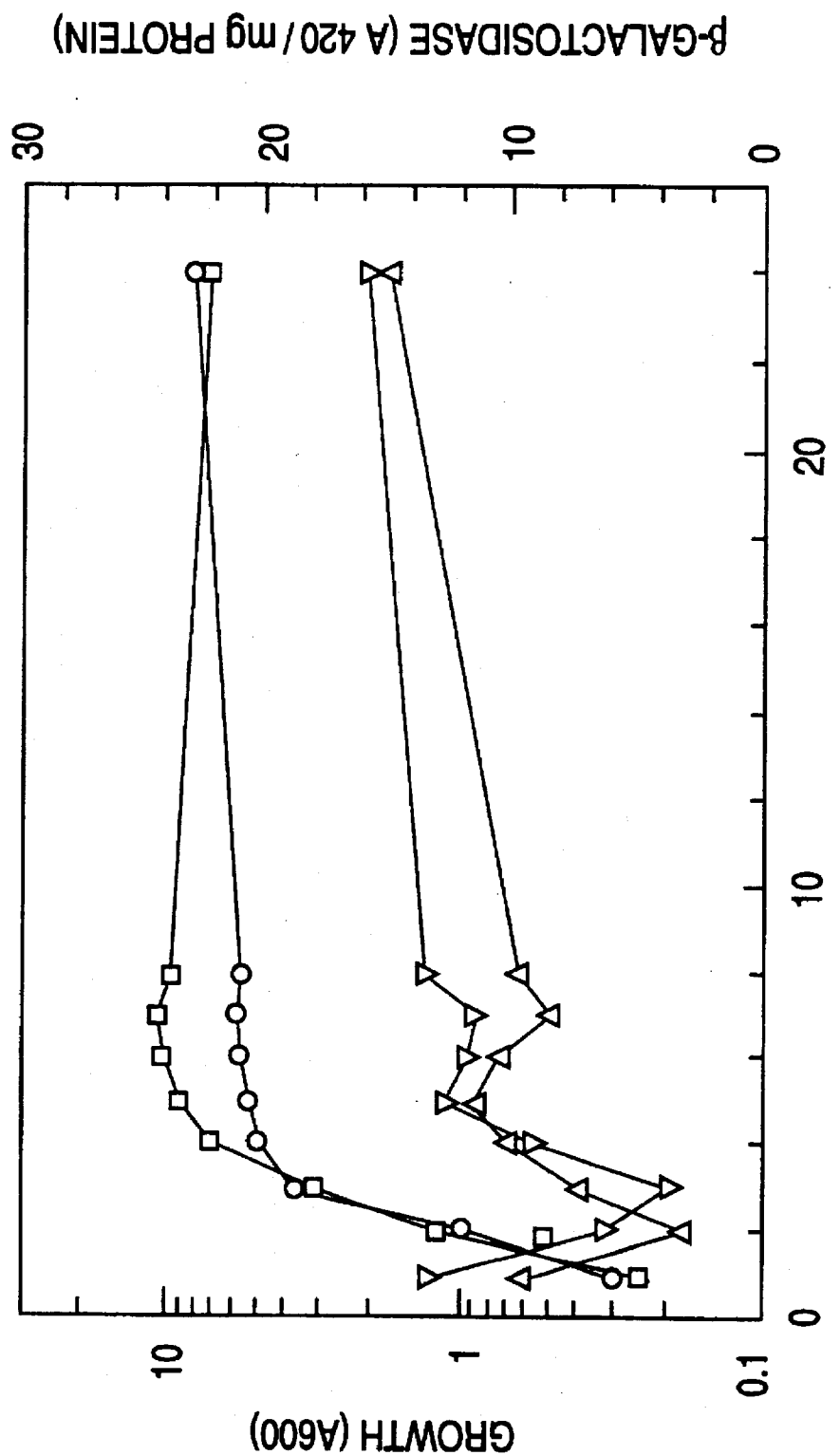
FIG. 7 is a graph depicting the effect of the TR1-5 mutation on the expression of a bolA::lacZ gene fusion. Sample identities are as described in the legend to FIG. 2, except that the genetic background of the strains was ZK916, which contains a chromosomally encoded bolA-lacZ fusion.

The gene bolA has been shown to directly influence the change in cell size which occurs during entry into stationary phase. Bohannen et al. (1991). Comparison of bolA expression in TR1-5 and wild-type strains grown in Kornberg medium revealed that the TR1-5 mutation does not significantly alter the level of bolA expression (FIG. 7). Therefore, the significant difference in size between the two strains appears not to be mediated via regulatory effects on the expression of bolA and perhaps is simply an indirect effect of csrA on endogenous glycogen levels.

EXAMPLE 7

Molecular cloning and nucleotide sequence of the native and TR1-5 mutant alleles of csrA For the experiments described in this Example and in the Examples above, standard procedures were used for isolation of chromosomal DNA, plasmid DNA, and restriction fragments, restriction mapping, transformation, and molecular cloning, according to methods previously described. Romeo et al (1988); and Romeo and Preiss (1989). Polymerase chain reaction (PCR) was conducted by the asymmetric synthesis method according to the method described by Gyllensten (1989) In Erlich (ed.), *PCR Technology: Principles and Applications for DNA Amplification*, MacMillan, N.Y., pp. 45–60. Deletion mutants of pCSR10 were constructed according to the method described by Henikoff (1984) *Gene* 28:351–359. Nucleotide sequencing was performed by the dideoxynucleotide chain termination method according to the method of Sanger et al. (1977) *Proc. Natl. Acad. Sci. USA* 74:5463–5467.

For obtaining the nucleotide sequence of CsrA, both strands of DNA were sequenced in their entirety with double-stranded plasmid DNA or single-stranded PCR products as the template. Overlap between all contiguous sequences was obtained, and the region of the TR1-5 insertion was sequenced from both the mutant and wild-type csrA alleles. DNA and protein sequence analyses were routinely conducted by using the software DNA Strider. Marck (1988) *Nucl. Acids Res.* 16:1829–1836. Searches for homologous genes, proteins, and motifs in the EMBL and GenBank, SwissProt, and Prosite data bases, respectively, were conducted by using the Wisconsin Genetics Computer Group software package developed by the University of Wisconsin Biotechnology Center (Madison, Wis.).

Radioisotopically labeled $^{32}pp_i$ (2.1 mCi/μmol) and α-$^{35}$S-dATP (1,200 mCi/μmol) were purchased from Dupont NEN (Wilmington, Del.). Sequenase 2.0 enzyme and other reagents for DNA sequence analysis were purchased from U.S. Biochemical Corp. (Cleveland, Ohio). Exonuclease III and mung bean nuclease were purchased from New England Biolabs (Beverly, Mass.). Protein and DNA molecular weight standards were from Bethesda Research Laboratories (Bethesda, Md).

The TR1-5 mutant allele of CsrA was cloned by ligating restriction fragments from a partial Sau3A1 digest of chromosomal DNA obtained from a secondary P1vir transductant of the TR1-5 mutation (TR1-5BW3414) into the BamHI site of pUC19 and selecting for Kan$^r$ Amp$^r$ transformants of HB101. Five plasmid clones containing the TR1-5 mutation were isolated, including pTR151.

Figure 8:
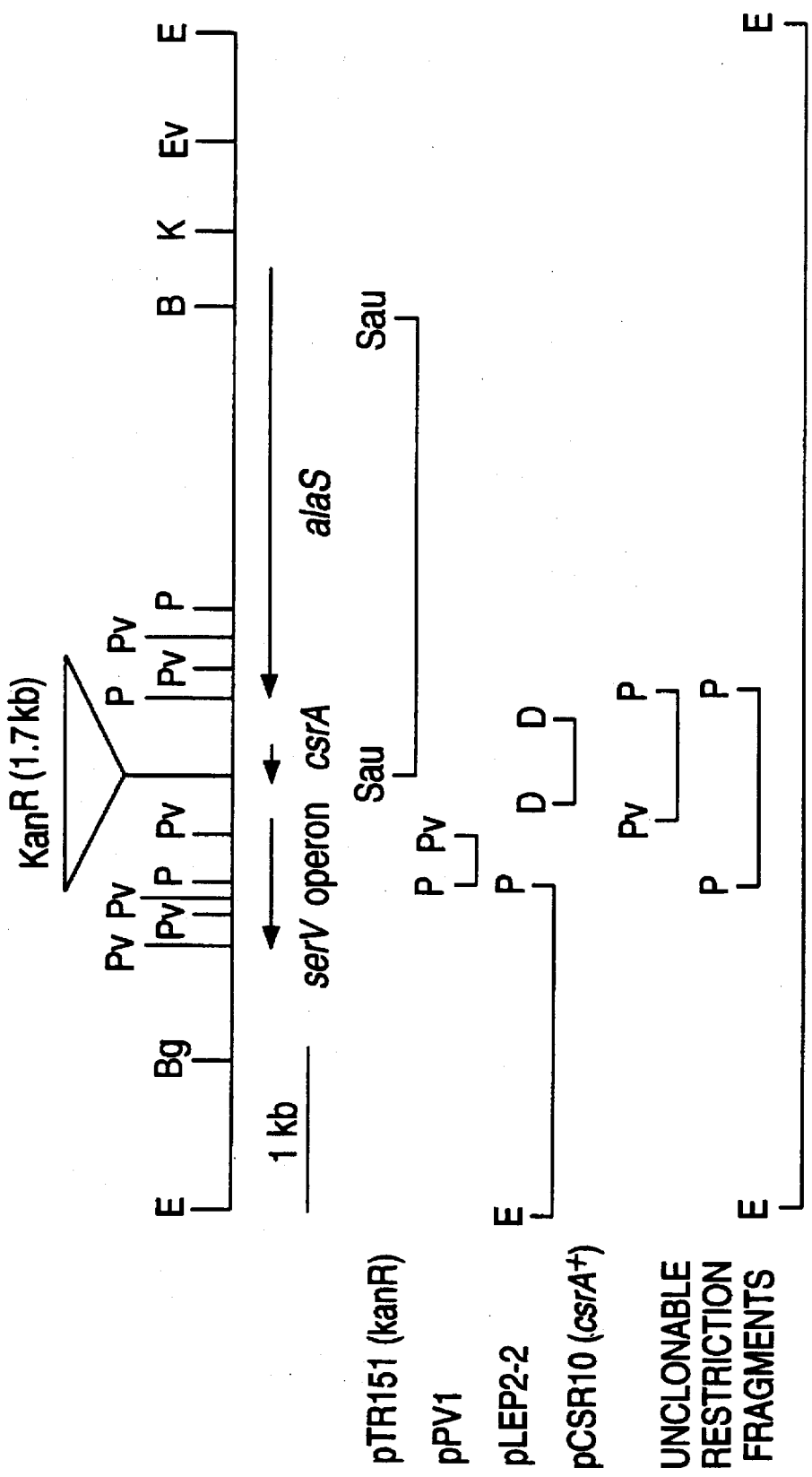
FIG. 8 depicts the restriction endonuclease sites of plasmid clones isolated from the region of csrA. Restriction sites are as follows: B, BamHI; Bg, BglI; D, DdeI; E, EcoRI; Ev, EcoRV; K, KpnI; P, PstI; Pv, PvuII; Sau, Sau3A1.

The nucleotide sequence of pTR151 was determined (FIGS. 8 and 9). The accession number L07596 has been assigned to the sequence shown in FIG. 9 by GenBank, which has been recorded in a data base of *E. coli* sequences compiled by Rudd et al. (1991). Subclones derived from this plasmid were used to search the EMBL and GenBank data bases for homologous genes. This search showed that the Kan$^r$ marker had been inserted downstream from alaS, which encodes alanine tRNA synthetase. Putney et al. (1981). None of the Kan$^r$ plasmid clones that were isolated contained csrA DNA from the side of the marker opposite alaS.

Attempts to subclone the entire region of the native csrA gene directly from a bacteriophage λ clone (λ446 of the Kohara miniset) into pUC19 or pLG339 were unsuccessful, although numerous plasmid clones containing restriction fragments that originated near this region were isolated. Restriction fragments from a Sau3A1 digest of chromosomal DNA from *E. coli* strain TR1-5BW3414 were cloned into the vector pUC19 to generate pTR151. The plasmid clones pPV1, pLEP2-2, and pCSR10 were generated by subcloning the indicated restriction fragments derived from λ446 into pUC19. Two of these clones, pPV1 and pLEP2-2 (FIG. 8), were partially sequenced and were found to contain part of the serV operon of tRNA genes Komine et al. (1990). These sequence data and the restriction map of *E. coli* K-12 (Rudd et al. (1991)) indicated that approximately 0.2 kb of DNA sequence remained undetermined on the counterclockwise side of the Kan$^r$ marker, i.e., between serV and the kanR gene. Each strand of DNA in this region was individually amplified from λ446 DNA by asymmetric PCR according to the method described by Gyllensten (1989). Thus, the nucleotide sequence of both strands of the 0.7-kb gap separating the alas and serV genes on the *E. coli* K-12 chromosome was determined, and the region of the TR1-5 transposition mutation was sequenced from both the mutant and the wild-type csrA alleles.

The largest open reading frame (ORF) observed between alas and serV was capable of encoding only a 61 amino acid polypeptide (FIG. 9). This was the only ORF in this region that was preceded by sequence motifs that are characteristic of a ribosome-binding site (Shine and Dalgarno (1974)), and it displayed a consensus sequence in the initiation codon-distal region that is typical of genes that are translated in *E. coli*. Petersen et al. (1988). The transposition site is located at codon 51 of this ORF. There is no obvious rho-independent terminator sequence for this proposed gene (FIG. 9), although a potential stem and loop structure was found immediately following alaS. Computer-assisted searches with the nucleotide sequence of this ORF or the deduced amino acid sequence of its proposed gene product failed to identify homologous genes, proteins, or procaryotic sequence motifs. The deduced amino acid sequence of the ORF contained no cysteine, phenylalanine, or tryptophan. Analysis of this amino acid sequence to predict hydrophobicity according to the method described by Kyte and Doolittle (1982) *J. Mol. Biol.* 157:105–132 indicated that the N-terminal half of the proposed product is hydrophobic, while the C-terminal half is relatively hydrophilic.

Since the inspection of clonable versus unclonable fragments in the region of csrA (FIG. 8) indicated that an element in the region of the serV promoter, perhaps the promoter itself, was not amenable to plasmid cloning, a 0.53-kb DdeI restriction fragment that avoided the intact serV promoter (FIGS. 8 and 9) but contained the proposed csrA coding region was isolated from λ446, made blunt ended with the Klenow fragment, and subcloned into the SmaI site of pUC19 to generate pCSR10.

The nucleotide sequence of the region between the alas and serV genes on the *E. coli* K-12 genome is shown in FIG. 9. Three bases are shown in boldface type in the alas region to indicate discrepancies with the previously published sequence. Putney et al. (1981) *Science* 213:1497–1501. The proposed ribosome-binding region (Shine-Dalgarno [S.D.]) of csrA, the −10 and −35 regions of serV, and an inverted repeat sequence immediately downstream from alas are underlined. Shine and Dalgarno (1974) *Proc. Natl. Acad. Sci. USA* 71:1342–1346; and Komine et al. (1990) *J. Mol. Biol.* 212:579–598. Nucleotides 283 to 286 are complementary to nucleotides near the 5' terminus of *E. coli* 16S RNA and fulfill the criteria for sequences which are expected to be found within the initiation codon-distal region of expressed genes. Petersen et al. (1988) *EMBO J.* 7:3957–3962.

Figure 10:
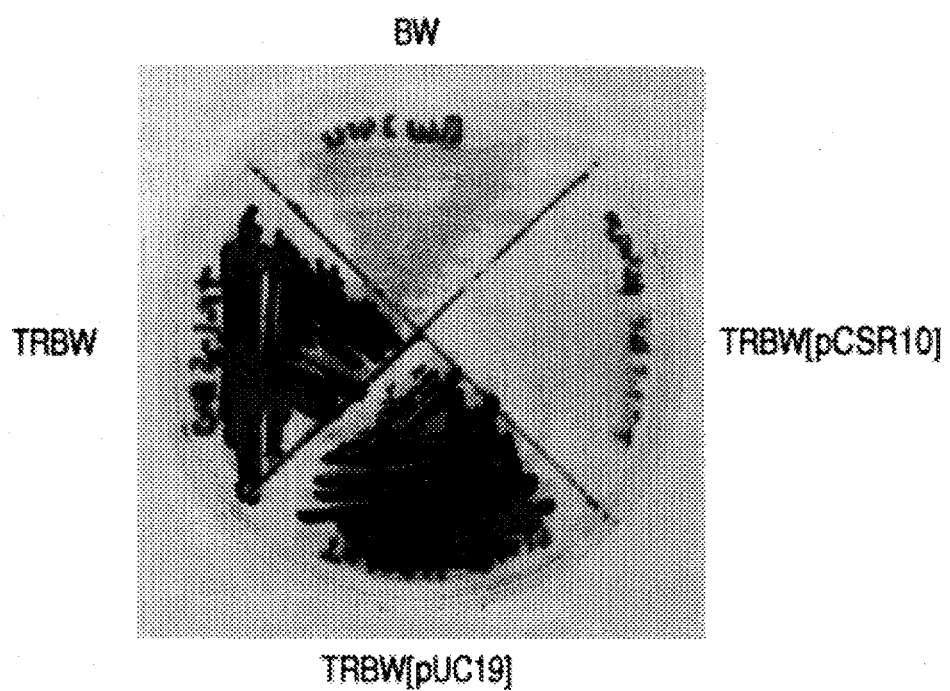
FIG. 10 shows the growth patterns of various cell lines indicating that pCSR10 strongly inhibits glycogen biosynthesis in vivo. Abbreviations: BW, BW3414; TRBW, TR1-5BW3414.

The glycogen-overproducing mutant TR1-5BW3414 was transformed with pCSR10 and transformants were streaked onto Kornberg medium and incubated overnight at 37° C. before staining with iodine. Transformation of TR1-5BW3414 with pCSR10 had a dramatic effect on glycogen accumulation (FIG. 10). A variety of *E. coli* strains have been transformed with the plasmid pCSR10, and in all cases the transformants have been found to be deficient in glycogen. These results indicate that pCSR10 contains the functional csrA gene.

EXAMPLE 8

Figure 11B:
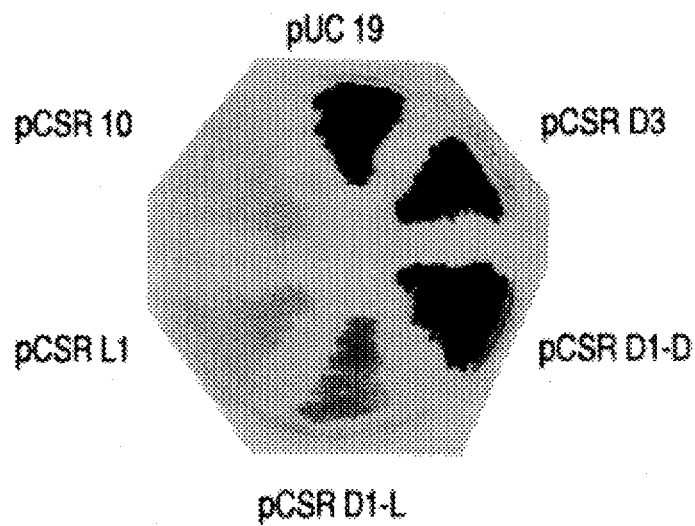

Complementation and in vitro expression studies of csrA: evidence that csrA encodes a 61 amino acid polypeptide that inhibits glycogen biosynthesis Several deletion derivatives of pCSR10 were constructed and sequenced to allow analysis of the proposed csrA coding region (FIG. 11). A 57-bp deletion that is positioned 94 bp downstream from the coding region did not affect the ability of plasmid pCSR-L1 to complement the TR1-5 mutation. A deletion that removed 8 amino acids of the coding region and resulted in the addition to 24 heterologous amino acids had a slight effect on the ability of plasmid pCSR-D1-L to alter the glycogen synthesis phenotype. Finally, two deletions that remove 21 or 16 amino acids from the proposed csrA coding region severely disrupted the ability of plasmids pCSR-D3 and pCSR-D1-D, respectively, to complement the TR1-5 mutation. These analyses show that disruption of the 3' end of the ORF that was proposed to encode csrA interferes with the effect of these plasmids on the glycogen phenotype. The observation that removing 8 amino acids of the coding region only partially inactivates csrA in a multicopy plasmid indicates that a partially active product could also be produced from the TR1-5 mutant allele (an insertion at codon 51). In the latter case, the negative effect of the mutant gene product on glycogen synthesis may be minimal or negligible, since it should be expressed at a much lower level.

Figure 11C:
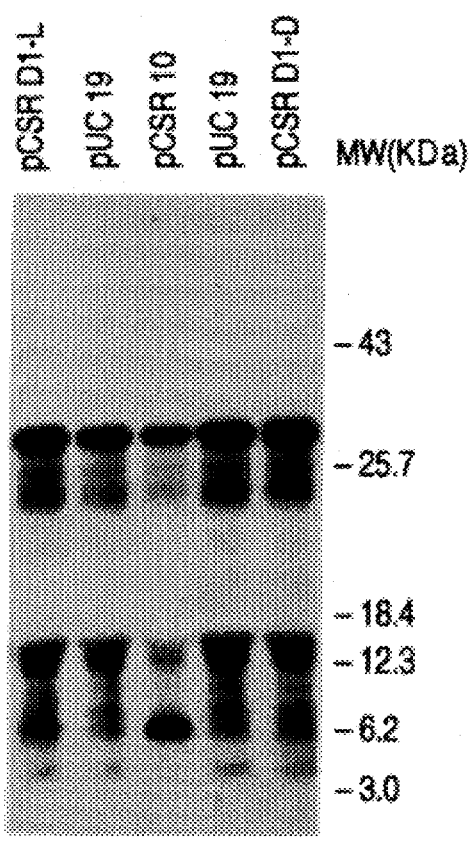

The proteins encoded by pUC19, pCSR10, and two of the deletion derivatives that alter the proposed coding region of csrA were examined by expression of the plasmid-encoded genes in S-30-coupled transcription translation reactions and analysis of the in vitro-synthesized proteins as previously described by Romeo and Preiss (1989) (FIG. 11C). Briefly, proteins were labeled with [$^{35}$S]methionine, separated on 10 to 22% gradient sodium dodecyl sulfate (SDS)-polyacrylamide slab gels, and detected by fluorography with sodium salicylate according to the method described by Chamberlain (1979) Anal. Biochem. 98:132–135. The results obtained indicated that pCSR10 encoded only a single polypeptide that was not observed in the reaction with pUC19 as a template (FIG. 11C). This polypeptide was strongly expressed in vitro and exhibited a mobility on SDS-polyacrylamide gel electrophoresis that was consistent with the molecular mass of the proposed csrA gene product, 6.8 kDa. One of the deletions (present in pCSR-D1-L) resulted in a net change of +16 amino acids in the coding region, and the second (pCSR-D1-D) resulted in a net change of –12 amino acids. The pUC19-independent (insert-specific) proteins that were expressed from these deletion derivatives were detected in significantly lower levels than the insert-specific protein expressed from pCSR10, making interpretations about these deletions less than definitive. However, insert-specific proteins consistent with an increase (pCSR-D1-L) or a decrease (pCSR-D1-D) in gene product size, predicted by ORF analysis, were weakly detectable, indicating that the observed 183-bp ORF encodes the native csrA gene product. The poor expression of the two deletion derivatives could be due to effects of the deletions on transcript or protein stability. Alternatively, one or more regulatory sites for csrA expression may be located distal to the csrA coding region.

Taken together, these experiments provided both structural and functional evidence that the proposed 183-bp ORF represents the csrA coding region and that the regulatory effects of csrA on glycogen biosynthesis are mediated via its 61 amino acid gene product.

EXAMPLE 9

Effects of csrA on cultures under varied growth conditions: anaerobiosis and sole carbon sources The TR1-5 mutant, isogenic csrA$^+$ (BW3414), and pCSR10-containing strains were grown on solid media under a variety of conditions and stained with iodine vapor to observe the effect of the csrA gene on glycogen biosynthesis. Strains grown anaerobically on Kornberg medium revealed iodine-staining properties that were at least as distinct as, or probably more so, than those of colonies grown aerobically, i.e., the mutant stained dark brown within seconds, whereas the wild-type and pCSR10-containing strains only stained yellow over two or more minutes of exposure to iodine vapor. This indicated that csrA-mediated regulation of glycogen synthesis is important under both aerobic and anaerobic conditions.

Under aerobic conditions on a rich defined medium, supplemented MOPS medium, the TR1-5 mutation (in the BW3414 genetic background) resulted in enhanced iodine staining on glucose, fructose, and glycerol. Glycogen levels were negligible, as indicated by yellow iodine staining, when the TR1-5 mutant and csrA$^+$ strains were grown on acetate or succinate.

Surprisingly, the pCSR10-containing strain grew as pinpoint colonies on MOPS medium when sodium succinate was added as the major carbon source, although it grew well on all other carbon sources tested, including sodium acetate. The wild-type (BW3414), TR1-5 mutant, and pUC19-containing strains grew well on sodium succinate. This indicates that overexpression of csrA results in a specific defect in the ability of cells to utilize succinate as a carbon source.

When wild-type, TR1-5, and pCSR10- or pUC19-containing strains (in the CF1648 genetic background) were streaked onto M9 minimal medium, it was found that the pCSR10-containing strain was unable to grow on any gluconeogenic substrates that were tested, including succinate, glycerol, pyruvate, and L-lactate, although it grew well on glucose and fructose, and although the wild-type and TR1-5 mutant strains grew on all of these substrates.

EXAMPLE 10

The csrA gene affects cell surface properties

Figure 12:
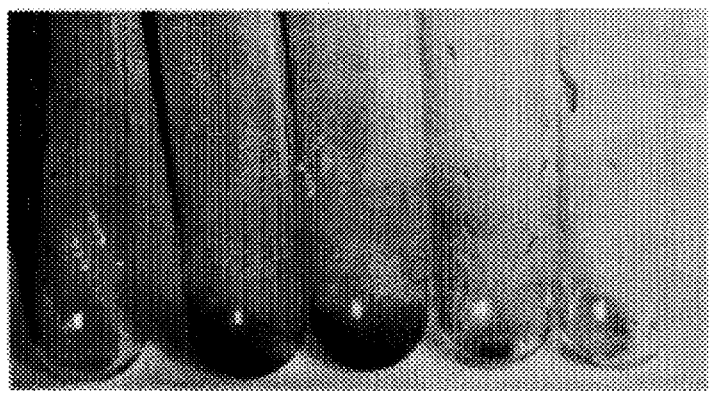
FIG. 12 depicts csrA cells which adhere tightly to borosilicate glass culture tubes. Strains: BW3414 (BW), TR1-5BW3414 (TR), TR1-5BW3414 [pUC19] (TR pUC19), or TR1-5BW3414[pCSR10] (TR pCSR10). Control: uninoculated medium.

Strains BW3414, TR1-5BW3414, TR1-5BW3414 [pUC19], or TR1-5BW3414[pCSR10] were grown overnight anaerobically without shaking in supplemented MOPS medium. Wanner et al. (1977). Culture tubes were treated with Gram's safranin to stain adherent cells and were rinsed three times with deionized water. The control tube contained uninoculated medium. The TR1-5 mutant grown under anaerobic conditions in liquid MOPS was found to be strongly adherent to glass culture tubes (FIG. 12). The isogenic wild-type parent was nonadherent, and the adherent phenotype of TR1-5 was abolished by pCSR10, confirming that the csrA mutation caused this phenotype.

EXAMPLE 11

Regulatory effects of csrA on intermediary carbon metabolism

In order to determine the effect of csrA expression on intermediary carbon metabolism in strains of E. coli K-12, the following experiments were performed. The cells were grown in Kornberg medium with 0.5% glucose at 37° C. with rapid gyratory shaking. For reference, FIG. 13 depicts the metabolic pathways effected by csrA expression, both positively and negatively.

Expression of glgA was measured indirectly by measuring β-galactosidase expression under the control of the glgA promoter. The TR1-5 mutation was P1-transduced according to the method described by Miller (1972) into DW18 (glgS::lacZ). Hengge-Aronis et al., Molec. Microbiol. (1992) 6:1877–1886. β-galactosidase activity was measured according to the method described by Romeo et al. Curr. Microbiol. (1990) 21:131–137.

Figure 14:
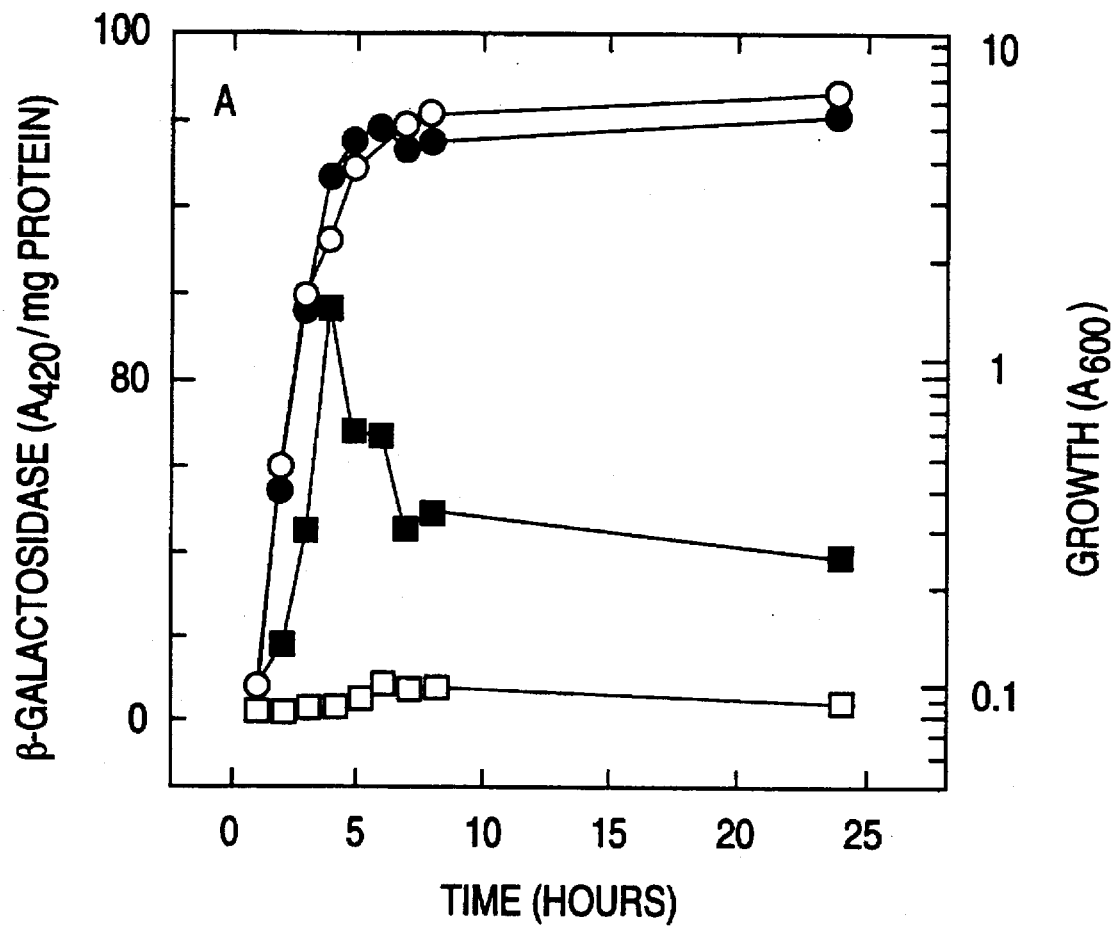
FIG. 14 is a graph depicting expression of a glgA-lacZ translational fusion in csrA+ (DW18) and csrA−, csrA−::kanR (TR1-5DW18) strains of E. coli K12. Symbols are as follows: csrA+ (open symbols); csrA− (closed symbols); circles (A600, depicting growth rate); and squares (enzymatic activity).

The results obtained are depicted in FIG. 14. The growth rate of the cell strains was determined by measuring turbidity at A600 and did not differ between the strains. β-galactosidase activity measured as A420/mg protein, was clearly expressed at a high level in the csrA− strain at the initiation of the stationary phase (closed squares) and only weakly expressed in the csrA+ strain (open squares). Thus, elimination of csrA expression upregulates expression of the glgA gene.

Expression of glgS was measured indirectly by measuring β-galactosidase expression under the control of the glgS promoter. The glgS-lacZ fusion construct and transduction were performed as described by Hengge-Aronis et al., (1992).

Figure 15:
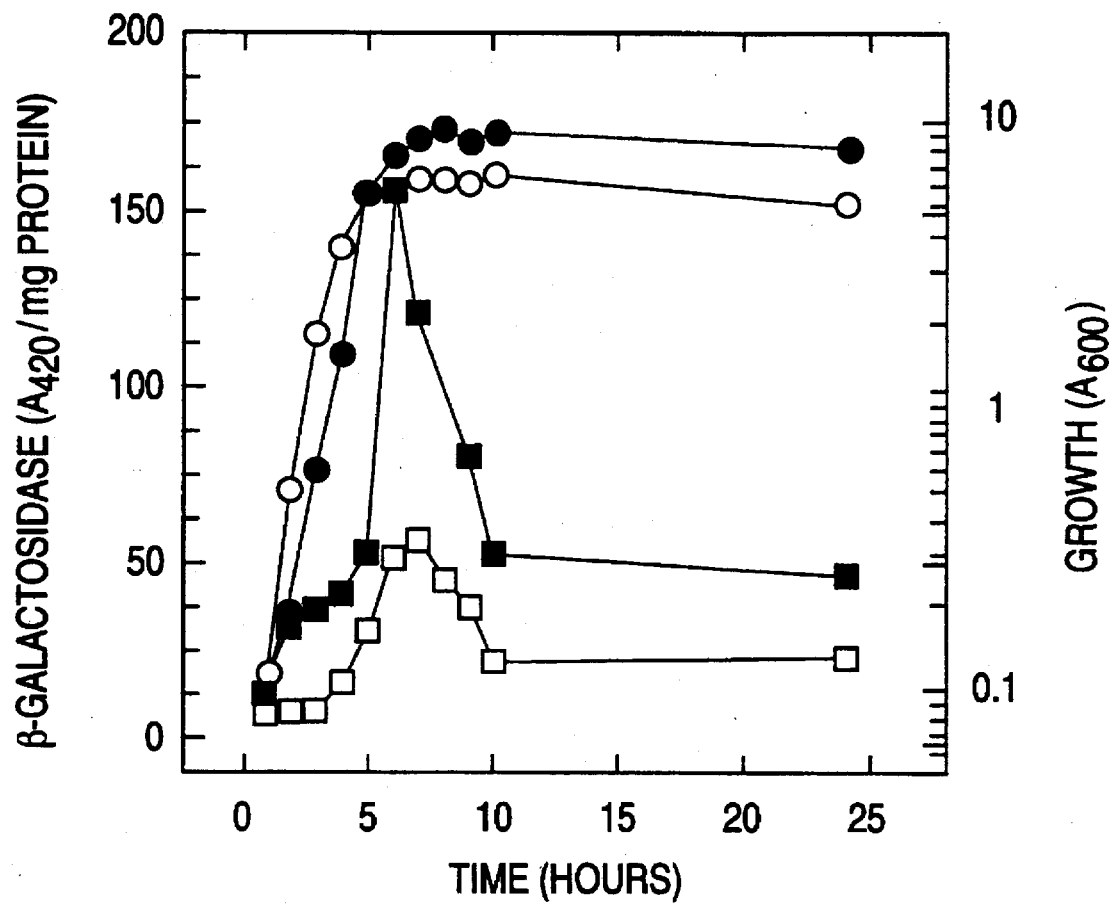
FIG. 15 is a graph depicting expression of a glgS-lacZ translational fusion in csrA+ (RH105) and, csrA−, csrA−::kanR (TR1-5RH105) strains of E. coli K-12. Symbols are the same as in FIG. 14.

The results obtained are depicted in FIG. 15. The growth rate did not differ between the strains but β-galactosidase expression in the csrA− strain was at least three fold higher at the initiation of the stationary phase (closed squares) than in the csrA+ strain (open squares). Thus, elimination of csrA expression upregulates expression of the glgS gene.

Figure 16:
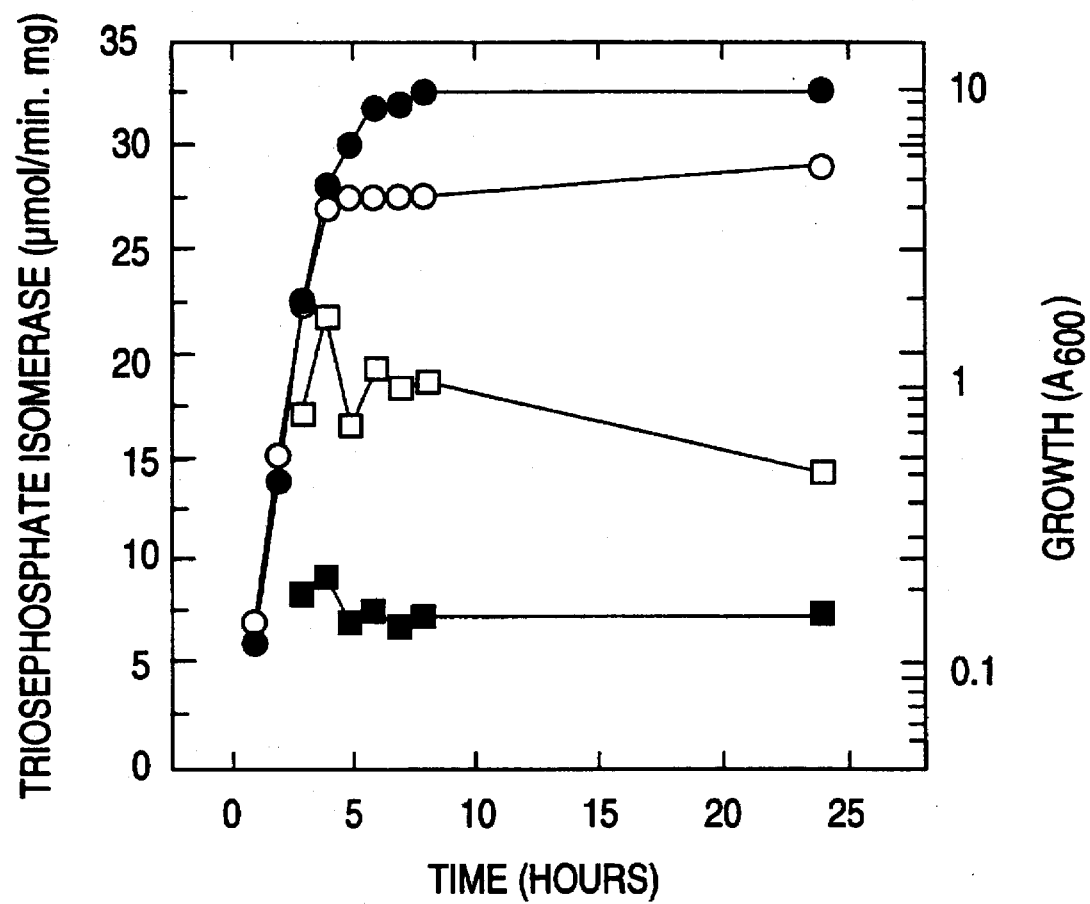
FIG. 16 is a graph depicting triosphosphate isomerase specific activity in extracts from BW3414 (csrA+) and TR1-5BW3414 (csrA−) strains of E. coli K-12. Symbols are the same as in FIG. 14.

Specific activity of triosephosphate isomerase was measured directly in cell extracts from a wild type, csrA+ strain (BW3414) and a csrA− strain TR1-5BW3414) according to the methods described by Esnouf et al. (1982) Met. Enzymol. 89:579–583; and Pompliano et al. (1990) Biochem. 29:3186–3194. The results obtained are shown in FIG. 16. The growth rate varied slightly between the strains and the level of triosephosphate isomerase activity, in µmol/min/mg was approximately four times higher in the csrA+ strain (open squares) than in the csrA− strain (closed squares). Thus elimination of csrA expression down regulates production of triosephosphate isomerase.

Figure 17:
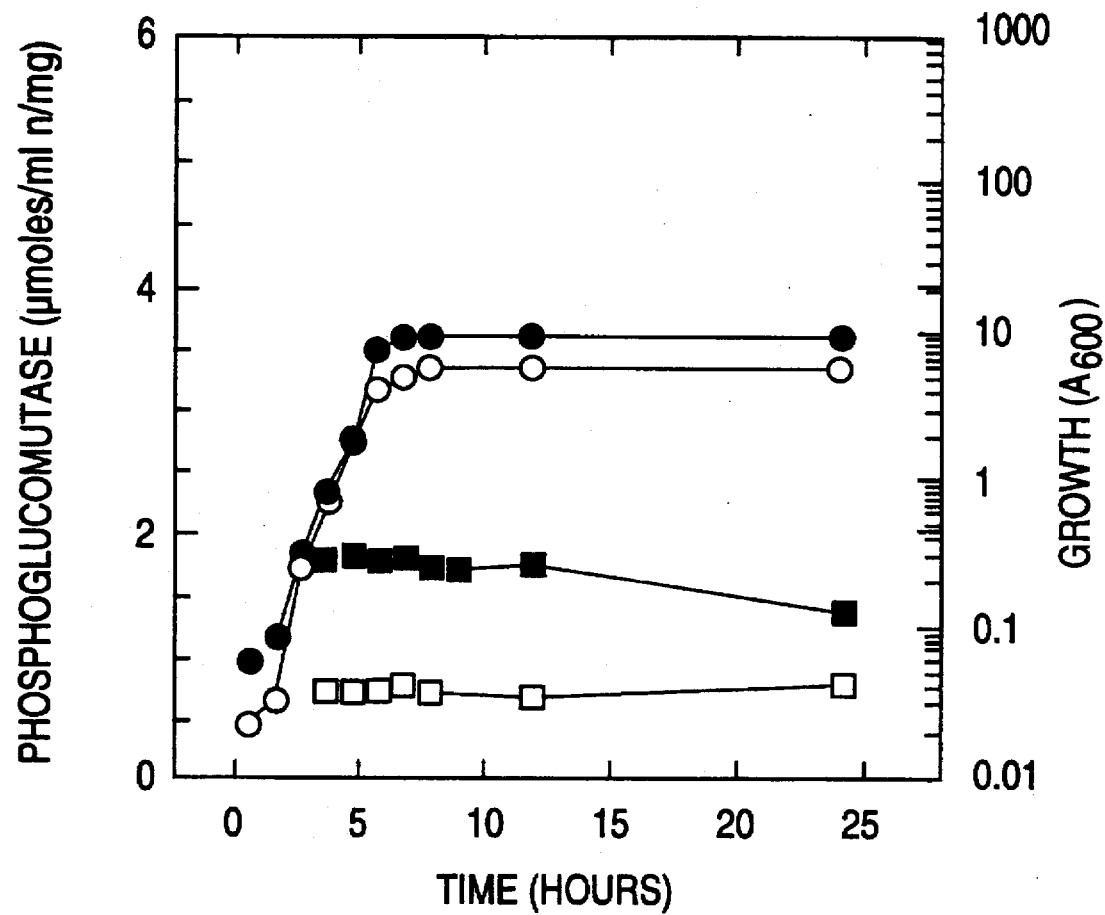
FIG. 17 is a graph depicting phosphoglucomutase specific activity in extracts from BW3414 (csrA+) and TR1-5 BW3414 (csrA−) strains of E. coli K-12. Symbols are the same as in FIG. 14.

Specific activity of phosphoglucomutase was measured directly in cell extracts from a wild type, csrA+ strain (BW3414) and a csrA− strain (TR1-5BW3414) according to the methods described by Pradel et al. (1991) Res. Microbiol. 142:37–45; and Adhya et al. (1971) J. Bacteriol. 108:621–626. The results obtained are shown in FIG. 17. The growth rate of the strains did not vary and the level of phosphoglucomutase activity, in µmol es/min/mg, was several fold higher in the csrA− strain (closed squares) than the csrA+ strain (open squares). This, elimination of csrA expression upregulates production of phosphoglucomutase.

Figure 18:
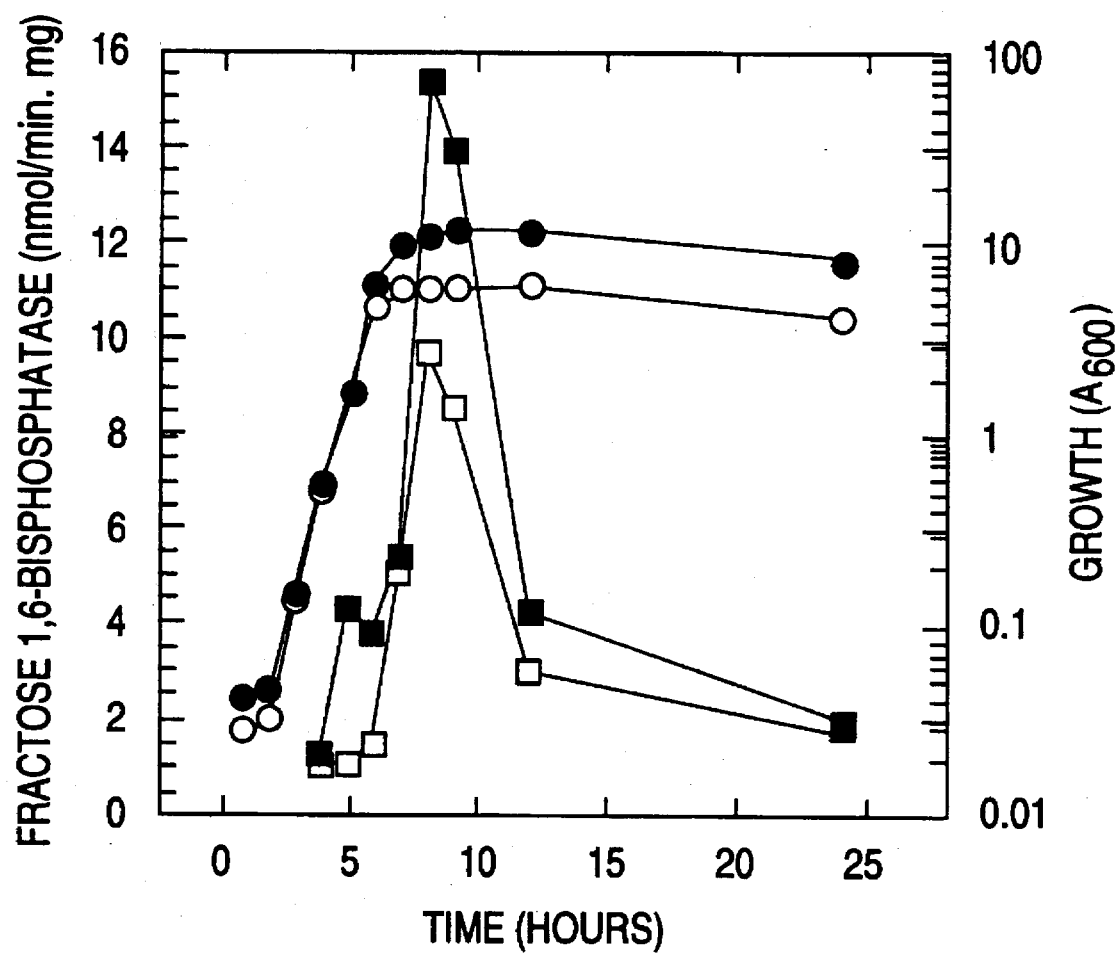
FIG. 18 is a graph depicting fructose-1,6-bisphosphatase specific activity in extracts from BW3414 (csrA+) and TR1-5 BW3414 (csrA−) strains of E. coli K-12. Symbols are the same as in FIG. 14.
Figure 19:
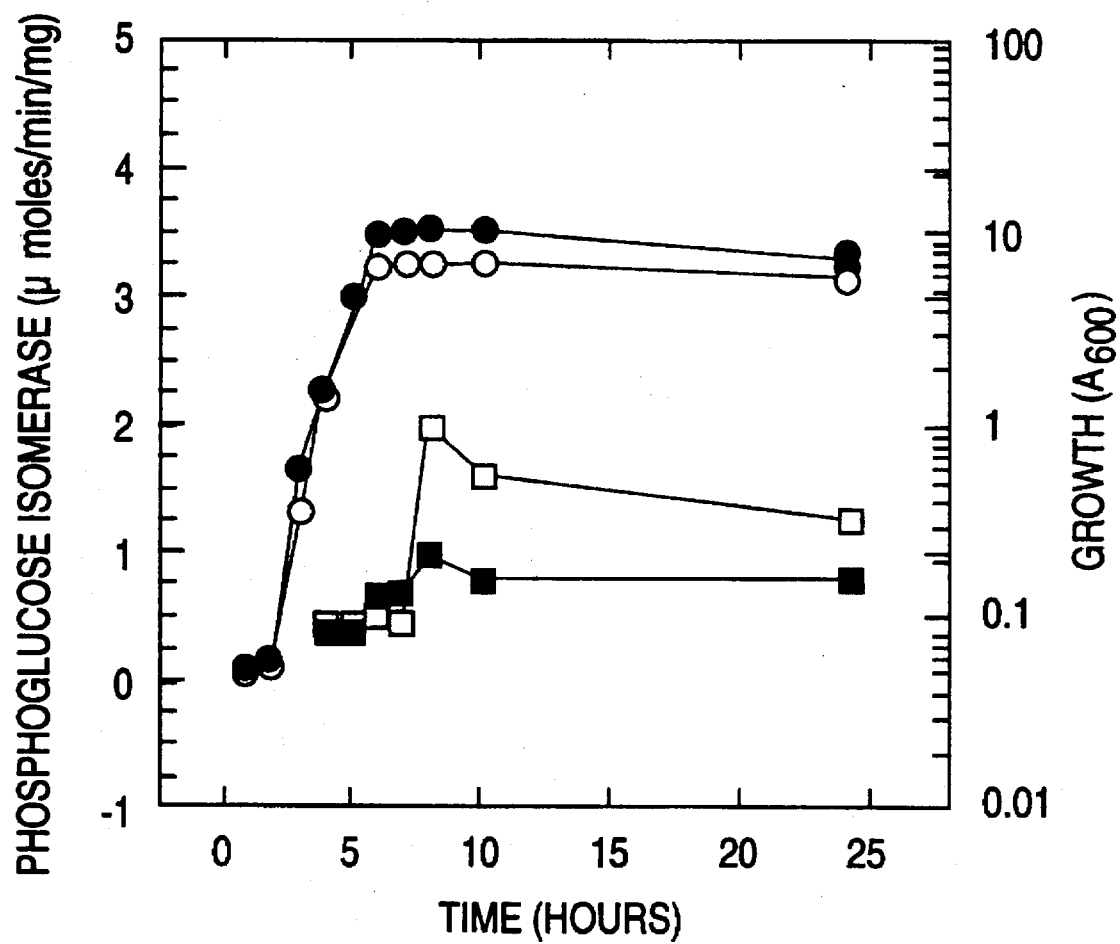
FIG. 19 is a graph depicting phosphoglucose isomerase specific activity in extracts from BW3414 (csrA+) and TR1-5 BW3414 (csrA−) strains of E. coli K-12. Symbols are the same as in FIG. 14.

Specific activity of fructose-1,6-bisphosphatase was measured directly in cell extracts from a wild type, csrA+, strain (BW3414) and a csrA− strain (TR1-BW3414) according to the method described by Fraenkel et al. (1965) J. Bacteriol. 90:837–842. The results obtained are shown in FIG. 18. The growth rate of the cells did not vary and the level of fructose-1,6-bisphosphatase activity, in µmol/min/mg, was substantially higher in the csrA− strain (closed squares) than in the csrA+ strain (open squares). Thus, elimination of csrA expression upregulates production of fructose-1,6-bisphosphatase.

Specific activity of phosphoglucose isomerase was measured directly in a wild type, csrA+, strain (BW3414) and a csrA− strain (TR1-5BW3414) according to the method described by Fraenkel et al. (1967) J. Bacteriol. 93:1571–1578. The results obtained are shown in FIG. 18. The growth rate of the strains did not vary and the level of phosphoglucose isomerase activity, in µmol/ml/min was a least two-fold higher in the csrA+ strain than in the csrA− strain. Thus, elimination of csrA expression decreases the level of phosphoglucose isomerase.

All publications and patent applications cited in this specification are incorporated herein by reference to the same extent as if each individual publication or patent application was specifically and individually indicated to be incorporated by reference.

Although the foregoing invention has been described in some detail by way of illustration and example for purposes of clarity and understanding, it will be apparent to those skilled in the art that certain modifications may be practiced. Therefore, the description and examples should not be construed as limiting the scope of the invention, which is delineated by the appended claims.

---

What is claimed is:

1. An isolated nucleic acid fragment comprising at least 15 nucleotides of the nucleotide sequence of bases 271–453 of SEQ ID NO: 1.

2. The nucleic acid fragment according to claim 1 wherein the nucleotide sequence is SEQ ID NO:1.

3. An isolated nucleic acid fragment encoding a csrA polypeptide having the amino acid sequence depicted in SEQ ID NO:3.

* * * * *